US008597632B2

(12) United States Patent
Kett et al.

(10) Patent No.: US 8,597,632 B2
(45) Date of Patent: Dec. 3, 2013

(54) ANIONIC OLIGOSACCHARIDE CONJUGATES

(75) Inventors: Warren Charles Kett, West Lebanon, NH (US); Deirdre Roma Coombe, Wembley Downs (AU)

(73) Assignee: Glycan Biosciences LLC, Corporate Centre, PA (US)

( * ) Notice: Subject to any disclaimer, the term of this patent is extended or adjusted under 35 U.S.C. 154(b) by 0 days.

(21) Appl. No.: 13/122,427

(22) PCT Filed: Oct. 2, 2009

(86) PCT No.: PCT/AU2009/001314
§ 371 (c)(1),
(2), (4) Date: Apr. 26, 2011

(87) PCT Pub. No.: WO2010/037180
PCT Pub. Date: Apr. 8, 2010

(65) Prior Publication Data
US 2011/0195025 A1 Aug. 11, 2011

Related U.S. Application Data

(63) Continuation of application No. PCT/AU2009/001314, filed on Oct. 2, 2009.

(30) Foreign Application Priority Data

Oct. 3, 2008 (AU) .............................. 2008905160

(51) Int. Cl.
*A61K 31/74* (2006.01)
(52) U.S. Cl.
USPC ..................................................... 424/78.17
(58) Field of Classification Search
None
See application file for complete search history.

(56) References Cited

U.S. PATENT DOCUMENTS

| 6,486,129 B1 | 11/2002 | Tromp et al. |
| 2007/0036867 A1 | 2/2007 | Mohapatra et al. |
| 2008/0146522 A1 | 6/2008 | Coombe et al. |

FOREIGN PATENT DOCUMENTS

| EP | 0649854 B1 | 3/2000 |
| WO | 9965934 A1 | 12/1999 |
| WO | 2005100374 A1 | 10/2005 |
| WO | 2007086923 A2 | 8/2007 |

OTHER PUBLICATIONS

International Search Report for PCT/AU2009/001314, Completed by the Australian Patent Office on Oct. 29, 2009, 2 Pages.
Adcock et al. "Glucocorticoid Pathways in Chronic Obstructive Pulmonary Disease Therapy", Proc Am Thorac Soc, 2005, vol. 2, p. 313-319.
Allen. "Effects of Inhaled Steroids on Growth, Bone Metabolism, and Adrenal Function", Advances in Pediatrics 2006, vol. 53, p. 101-110.
Anzueto. "Clinical Course of Chronic Obstructive Pulmonary Disease: Review of Therapeutic Interventions", The American Journal of Medicine 2006, vol. 119, No. 10A, p. S46-S53.
Ballantyne et al. "Blocking IL-25 prevents airway hyperresponsiveness in allergic asthma", J Allergy Clin Immunol Dec. 2007, vol. 120, No. 6, p. 1324-1331.
Barnes. "Mediators of Chronic Obstructive Pulmonary Disease", Pharmacological Reviews 2004, vol. 56, No. 4, p. 515-548.

(Continued)

*Primary Examiner* — Paul Dickinson
(74) *Attorney, Agent, or Firm* — Brooks Kushman P.C.

(57) ABSTRACT

The invention relates to anionic oligosaccharide conjugates that may be used to mimic the structure and/or activity of the anionic bioactive molecules known as glycosaminoglycans (GAGs).

25 Claims, 6 Drawing Sheets

(56) References Cited

OTHER PUBLICATIONS

Barnes. "Drugs for asthma", British Journal of Pharmacology 2006, vol. 147, p. S297-S303.
Barnes et al. "COPD: current therapeutic interventions and future approaches", Eur Respir J 2005, vol. 25, p. 1084-1106.
Blaiss. "Rhinitis-Asthma Connection: Epidemiologic and Pathophysiologic Basis", Allergy and Asthma Proc. Jan.-Feb. 2005, vol. 26, No. 1, p. 35-40.
Borish. "Allergic rhinitis: Systemic inflammation and implications for management", J Allergy Clin Immunol Dec. 2003, vol. 112, No. 6, p. 1021-1031.
Cepkova et al. "Pharmacotherapy of Acute Lung Injury and the Acute Respiratory Distress Syndrome", Journal of Intensive Care Medicine 2006, vol. 21, No. 3, p. 119-143.
Coombe et al. "Expressed luciferase viability assay (ELVA) for the measurement of cell growth and viability", Journal of Immunological Methods 1998, vol. 215, p. 145-150.
El-Shanawany et al. "Clinical Immunology Review Series: An Approach to the Patient with anaphylaxis", Clinical and Experimental Immunology 2008, vol.153, p. 1-9.
Fernig. "Optical Biosensor Techniques to Analyze Protein-Polysaccharide Interactions", Methods in Molecular Biology 2001, vol. 171, p. 505-518.
Gelfand. "Inflammatory mediators in allergic rhinitis", J Allergy Clin Immunol Nov. 2004, vol. 114, No. 5, p. S135-S138.
Golden. "What is anaphylaxis", Current Opinion in Allergy and Clinical Immunology 2007, vol. 7, p. 331-336.
Golightly et al. "Second-Generation Antihistamines. Actions and Efficacy in the Management of Allergic Disorders", Drugs 2005, vol. 65, No. 3, p. 341-384.
Green et al. "The Reclassification of Asthma Based on Subphenotypes", Curr Opin Allergy Clin Immunol. 2007, vol. 7, No. 1, p. 43-50.
Halpin el al. "Chronic Obstructive Pulmonary Disease", Proc. Am. Thorac. Soc. 2006, vol. 3, p. 619-623.
Heflin et al. "Heparin Reverses Anaphylactoid Shock in a Porcine Model", Annals of Emergency Medicine Aug. 2006, vol. 48, No. 2, p. 190-193.
Hymowitz et al. "IL-17s adopt a cystine knot fold: structure and activity of a novel cytokine, IL-17F, and implications for receptor binding", The EMBO Journal 2001, vol. 20, No. 19, p. 5332-5341.
Linden et al. "Neutrophils, interleukin-17A and lung disease", Eur. Respir. J. 2005, vol. 25, p. 159-172.
MacLaren et al. "Reviews of Therapeutics. Emerging Role of Anticoagulants and Fibrinolytics in the Treatment of Acute Respiratory Distress Syndrome", Pharmacotherapy 2007, vol. 27, No. 6, p. 860-873.
MacNee. "Pathogenesis of Chronic Obstructive Pulmonary Disease", Proc. Am. Thorac. Soc. 2005, vol. 2, p. 258-266.
Mortelliti et al. "Acute Respiratory Distress Syndrome", American Family Physician May 1, 2002, vol. 65, No. 9, p. 1823-1830.
Nielsen et al. "Comparison of Intranasal Corticosteroids and Antihistamines in Allergic Rhinitis", Am. J. Respir. Med. 2003, vol. 2, No. 1, p. 55-65.
Palmqvist et al. "Differential effects of fluticasone and montelukast on allergen-induced asthma", Allergy 2005, vol. 60, p. 65-70.
Passalacqua et al. "An Update on the Asthma-Phinitis Link", Curr. Opin. Allergy Clin. Immunol. 2004, vol. 4, No. 3, 8 Pages.
Pawankar. "Allergic Rhinitis and Asthma: The Link, The New ARIA Classification and Global Approaches to Treatment", Curr. Opin. Allergy Clin. Immunol. 2004, vol. 4, No. 1, 5 Pages.
Peavy et al. "Understanding the mechanisms of anaphylaxis", Curr. Opin. Allergy Clin. Immunol. 2008, vol. 8, No. 4, p. 310-315.
Sharkhuu et al. "Mechanism of interleukin-25 (IL-17E)-induced pulmonary inflammation and airways hyper-reactivity", Clinical and Experimental Allergy 2006, vol. 36, p. 1575-1583.
Simons. 9. Anaphylaxis:, J. Allergy Clin. Immunol. 2008, vol. 121, p. S402-S407.
Skoner. "Update of growth effects of inhaled and intranasal corticosteroids", Current Opinion in Allergy and Clinical Immunology 2002, vol. 2, p. 7-10.
Song et al. "IL-17-Producing Alveolar Macrophages Mediate Allergic Lung Inflammation Related to Asthma", J. Immunol. 2008, vol. 181, p. 6117-6124.
Sutherland et al. "Airway inflammation in chronic obstructive pulmonary disease: Comparisons with asthma", J Allergy Clin Immunol Nov. 2003, vol. 112, No. 5, p. 819-827.
Szilasi et al. "Pathology of Chronic Obstructive Pulmonary Disease", Pathology Oncology Research 2006, vol. 12, No. 1, p. 52-60.
Tamachi et al. "IL-25 enhances allergic airway inflammation by amplifying TH2 cell-dependent pathway in mice", J Allergy Clin Immunol Sep. 2006, vol. 118, No. 3, p. 606-614.
Walls et al. "Optimising the management of allergic rhinitis: an Australian persepective", MJA Jan. 3, 2005, vol. 182, No. 1, p. 28-33.
Wang et al. "The IL-17 cytokine family and their role in allergic inflammation", Current Opinion in Immunology 2008, vol. 20, p. 697-702.
Ware et al. "The Acute Respiratory Distress Syndrome", The New England Journal of Medicine May 4, 2000, vol. 342 No. 18, p. 1334-1349.
Wenzel. "Asthma: defining of the persistent adult phenotypes", Lancet 2006, vol. 368, p. 804-813.
Ogawa et al. "Mediators of Anaphylaxis", Immunol. Allergy Clin. N. Am. 2007, vol. 27, p. 249-260.
Yanez et al. "Intranasal corticosteroids versus topical H1 receptor antagonists for the treatment of allergic rhinitis: a systematic review with meta-analysis", Ann Allergy Asthma Immunol. 2002, vol. 89, p. 479-484.

`US 8,597,632 B2`

ANIONIC OLIGOSACCHARIDE CONJUGATES

CROSS-REFERENCE TO RELATED APPLICATION

This application is the U.S. national phase of PCT Application. No. PCT/AU2009/001314 filed Oct. 2, 2009, which claims priority to Australian application 2008905160 filed Oct. 3, 2008, the disclosures of which are incorporated in their entirety by reference herein.

FIELD OF THE INVENTION

The invention relates to anionic oligosaccharide conjugates that may be used to mimic the structure and/or activity of the anionic bioactive molecules known as glycosaminoglycans (GAGs). The invention also relates to the use of anionic oligosaccharide conjugates to probe the binding properties of GAGs and develop new improved biologically active agents. The invention also relates to processes for the preparation of the anionic oligosaccharide conjugates. Such anionic oligosaccharide conjugates are useful in the prophylaxis and/or treatment of disease conditions and in particular inflammatory respiratory disorders.

BACKGROUND TO THE INVENTION

Natural and synthetic anionic saccharide-based compounds continue to be used, and developed for use, as therapeutics. A well known example of such a compound is the natural product heparin which has been used clinically for over 80 years as an anticoagulant. Heparin has undergone two generations of improvements resulting in products with greater selectivity and/or specificity for the target. The first was a semi-synthetic process which generated a low molecular weight heparin displaying a greater specificity of action. The second approach involved a synthetic pentasaccharide which was selective for the target protein. The synthetic approach, however, consisted of approximately 40 chemical steps, highlighting the technical difficulty associated with the synthesis of such compounds.

One approach to overcoming the challenges posed by the synthesis of heparin, and GAGs more broadly, has been to target GAG mimetics. One class of such mimetics is the semi-synthetic sulfated natural homo-oligosaccharides. There is, however, disparity between the small size of the oligosaccharides that are readily accessed from natural sources and the independently selected from maltotriose, maltotetraose, maltopentaose, xylotetraose, xylopentaose, chitotetraose and chitopentaose which each comprise at least one anionic substituent such as a sulfate or phosphate substituent.

In another aspect the invention provides a process for preparing an anionic oligosaccharide of formula (I):

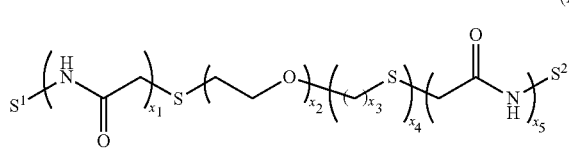

wherein:
  $S^1$ and $S^2$ each independently represent anionic oligosaccharides;
  $x_1$ represents an integer from 1 to 4;
  $x_2$ represents an integer from 0 to 11;
  $x_3$ represents an integer from 0 to 10;
  $x_4$ represents 0 or 1; and
  $x_5$ represents an integer from 1 to 4,
the process comprising the steps of:
  a) transforming each of the oligosaccharides into anionic oligosaccharides; and
  b) conjugating the oligosaccharides;
wherein steps a) and b) may be performed in either order.

In another aspect the invention provides the use of an anionic oligosaccharide of formula (I):

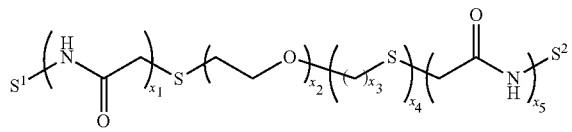

wherein:
  $S^1$ and $S^2$ each independently represent anionic oligosaccharides;
  $x_1$ represents an integer from 1 to 4;
  $x_2$ represents an integer from 0 to 11;
  $x_3$ represents an integer from 0 to 10;
larger oligo- and polysaccharides which produce activity in many biological systems. In particular, access to oligosaccharides comprising 6 or more monosaccharides, whilst maintaining the goals of structural diversity and low cost, is especially difficult.

There remains a continuing need to produce GAG mimetics which display a high degree of selectivity and/or specificity, and which are able to be produced by simple, cost effective methods.

SUMMARY OF THE INVENTION

In one aspect the invention provides an anionic oligosaccharide conjugate of formula (I):

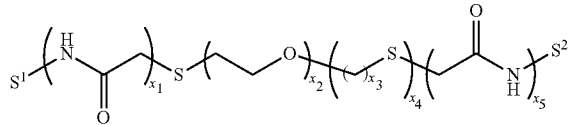

wherein:
  $S^1$ and $S^2$ each independently represent anionic oligosaccharides;
  $x_1$ represents an integer from 1 to 4;
  $x_2$ represents an integer from 0 to 11;
  $x_3$ represents an integer from 0 to 10;
  $x_4$ represents 0 or 1; and
  $x_5$ represents an integer from 1 to 4.

The anionic oligosaccharide conjugates of the present invention have substantial structural diversity and may be produced simply and efficiently. The length of the typically flexible linker between the anionic oligosaccharides may be tailored to mimic and/or determine spatial relationships between portions of GAGs that interact with a given molecular target, and accordingly in turn lead to the production of GAG mimetics that possess a high degree of selectivity and/or specificity.

In some embodiments $x_1$ and/or $x_5$ are 1 or 2, preferably 2. In some embodiments $x_2$ represents an integer from 0 to 4. In some embodiments $x_3$ is an integer from 2 to 6, preferably 2. In some embodiments $x_4$ is 1. In some embodiments $S^1$ and $S^2$ are $x_4$ represents 0 or 1; and
$x_5$ represents an integer from 1 to 4, in the prophylaxis and/or treatment of disease conditions, in particular inflammatory respiratory disorders.

In another aspect the invention provides the use of an anionic oligosaccharide of formula (I):

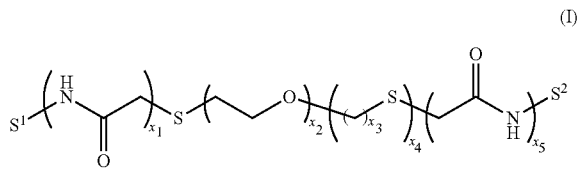

(I)

wherein:
$S^1$ and $S^2$ each independently represent anionic oligosaccharides;
$x_1$ represents an integer from 1 to 4;
$x_2$ represents an integer from 0 to 11;
$x_3$ represents an integer from 0 to 10;
$x_4$ represents 0 or 1; and
$x_5$ represents an integer from 1 to 4,
in an assay or screen.

In another aspect the invention provides an assay or screen for determining the biological effect of one or more anionic oligosaccharide conjugates, the assay comprising the steps of:

a) contacting a ligand, cell or animal with one or more anionic oligosaccharide conjugates each independently having the following formula (I):

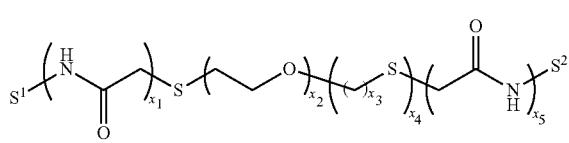

(I)

wherein:
$S^1$ and $S^2$ each independently represent anionic oligosaccharides;
$x_1$ represents an integer from 1 to 4;
$x_2$ represents an integer from 0 to 11;
$x_3$ represents an integer from 0 to 10;
$x_4$ represents 0 or 1; and
$x_5$ represents an integer from 1 to 4; and b) quantifying an effect of the one or more anionic oligosaccharide conjugates on the ligand, cell or animal.

In another aspect the invention provides a method of modulating the activity of a ligand comprising contacting the ligand with an anionic oligosaccharide conjugate of formula (I):

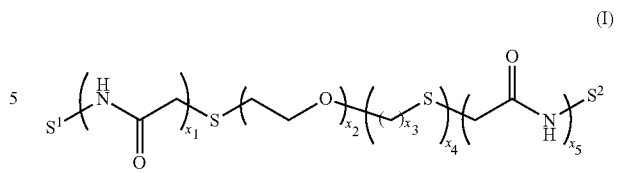

(I)

wherein:
$S^1$ and $S^2$ each independently represent anionic oligosaccharides;
$x_1$ represents an integer from 1 to 4;
$x_2$ represents an integer from 0 to 11;
$x_3$ represents an integer from 0 to 10;
$x_4$ represents 0 or 1; and
$x_5$ represents an integer from 1 to 4.

BRIEF DESCRIPTION OF THE FIGURES

Bud=Budesonide; D2=Anionic oligosaccharide conjugate ID 9; Drug concentrations 0.1 and 2.5 mg/kg.
** significantly different at P<0.01 from positive control
* significantly different at P<0.05 from positive control
++ significantly different from negative control

Bud=Budesonide; D2=Anionic oligosaccharide conjugate ID 9; Drug concentrations 0.1 and 2.5 mg/kg.
** significantly different at P<0.01 from positive control
* significantly different at P<0.05 from positive control
++ significantly different from negative control

Figure 1:
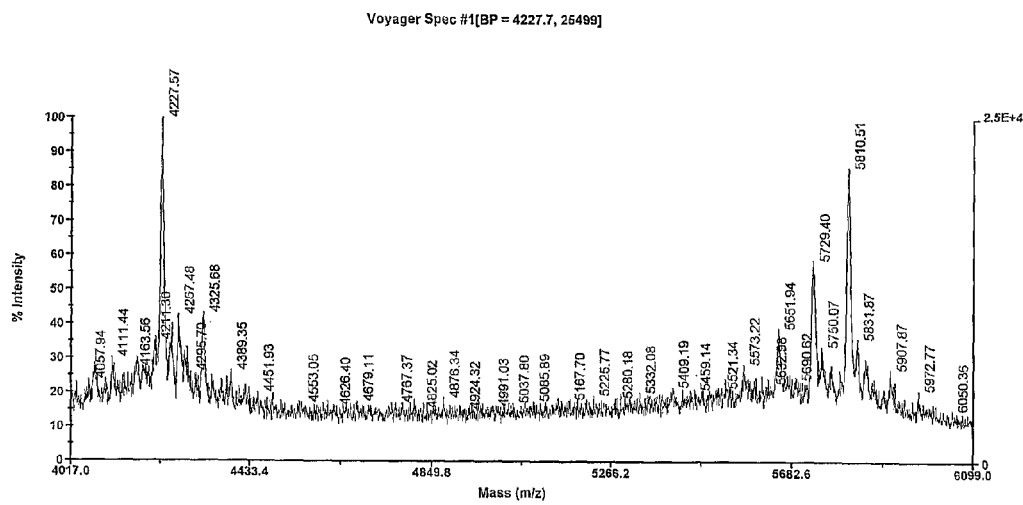
FIG. 1 shows MALDI-MS spectrum of N'-Fmoc-1-N-glycinamidomaltotrioside polysulfate using the technique of complexation with the peptide $(RG)_{19}R$. The mass of the major peak corresponding to the complex (5810.51) minus the peptide ion (4227.57) gives 1582.94 for the sulfated glycoconjugate (calc. for 10 O-sulfates is 1583.38).

Bud=Budesonide; D2=Anionic oligosaccharide conjugate ID 9; Drug concentrations 0.1 and 2.5 mg/kg.
*** significantly different at P<0.001 from positive control.
+++ Significantly different at P<0.001; ++ Significantly different at P<0.01 and + significantly different at P<0.05 from negative control.

DETAILED DESCRIPTION OF THE INVENTION

As used herein, the term "anionic" describes the net negative charge of a material. It will be understood that a given negatively charged material may have one or more positively charged counterions associated with it, or vice versa. In solution, a negatively charged material might dissociate from one or more positively charged counterions that it is associated with in the solid state. As used herein, the term "anionic" is used to describe a property of that material and not the overall complex with one or more counterions which will typically render the complex neutral. It is understood that certain functional groups are negatively charged, neutral or positively charged at varying values of pH. Whether a material is anionic will be determined based on the sum of these charges. Accordingly, at a given pH, if a material has one positively charged functional group and two negatively charged functional groups, then the material has a net negative charge and is anionic as the term is used in the context of the present invention. In preferred embodiments the conjugates of the present invention have a net negative charge in aqueous solution at a pH of 5. In preferred embodiments, the salts formed between the anionic oligosaccharide conjugates of the present invention and the one or more counterions are pharmaceutically acceptable salts.

Examples of functional groups that impart an anionic character onto the conjugates of the present invention are: sulfur based groups such as —$SO_2OH$, —$OSO_2OH$, —$OSO_2H$, —$SO_2H$ and —$OSO_2$—; and phosphorous based groups such as: —$OPO_2OH$, —$OP(S)(OH)_2$, —$OP(O)(OR)_2$, —$OP(S)(OR)_2$, —$OP(O)OHR$, —$OP(S)OHR$, —$OP(O)OR_1R_2$, —$OP(S)OR_1R_2$, —$OP(S)(OH)(SH)$ and cyclic phosphate. It will be understood that a number of the functional groups above may be readily deprotonated and will become anionic in aqueous solution at, for example, a pH of 5. Other functional groups shown above are neutral (e.g. —$OSO_2$— and —$OP(O)(OR)_2$) and accordingly can be used in combination with anionic functional groups to control the degree of anionic character present within the conjugate.

Preferred anionic derivatives of hydroxyl groups include sulfate and phosphate groups. In particular, it will be understood that in aqueous solution at pH 5, sulfate and phosphate groups are anionic groups as defined herein.

As used herein the term oligosaccharide refers to a carbohydrate that may contain any number of monosaccharide units, such as from 2 to 10 monosaccharide units, connected by alpha- and/or beta-glycosidic linkages. For example the oligosaccharide may comprise between 2 and 6 monosaccharide units.

Examples of monosaccharides are erythrose, threose, ribose, arabinose, xylose, lyxose, allose, altrose, glucose, mannose, gulose, idose, galactose and talose.

Examples of oligosaccharides comprising 2 or more monosaccharides are lactose, sucrose, amylose, the cello-oligosaccharides, the malto-oligosaccharides [such as maltose, maltotriose (O-α-D-glucopyranosyl-(1→4)-O-α-D-glucopyranosyl-(1→4)-D-glucopyranose), maltotetraose (O-α-D-glucopyranosyl-{(1→4)—O-α-D-glucopyrano-syl}$_2$-(1→4)-D-glucopyranose) and maltopentaose (O-α-D-glucopyranosyl-{(1→4)—O-α-D-glucopyranosyl}$_3$-(1→4)-D-glucopyranose)], the dextro-oligosaccharides, the chito-oligosaccharides, the xylo-oligosaccharides, manno-oligosaccharides (such as those produced by the hydrolysis of mannans, including yeast mannans) and the β1,3-gluco-oligosaccharides.

Preferred oligosaccharides for use in the present invention are the malto-oligosaccharides (such as maltotriose, maltotetraose and maltopentaose), the chito-oligosaccharides (such as chitotetraose and chitopentaose) and the xylo-oligosaccharides (such as xylotetraose and xylopentaose).

In one aspect the invention provides an anionic oligosaccharide conjugate of formula (I):

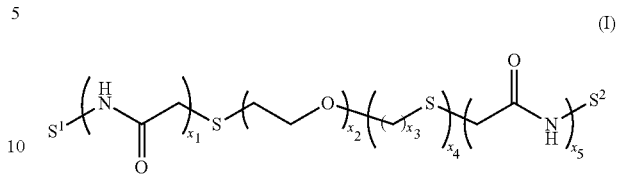

wherein:

$S^1$ and $S^2$ each independently represent anionic oligosaccharides;

$x_1$ represents an integer from 1 to 4;

$x_2$ represents an integer from 0 to 11;

$x_3$ represents an integer from 0 to 10;

$x_4$ represents 0 or 1; and $x_5$ represents an integer from 1 to 4.

The anionic oligosaccharides ($S^1$ and $S^2$) of formula (I) are covalently conjugated to each other through at least one sulfur atom which forms part of that portion of the conjugate that is between the anionic oligosaccharides which is referred to herein as the "linker". In the anionic oligosaccharide conjugates of the present invention, the linker moiety may also be referred to as the aglycone portion. The linker may affect the size, flexibility or rigidity, hydrophilicity and hydrophobicity of the anionic oligosaccharide conjugate. Accordingly, the linker is preferably chosen to maximize a given biological effect. Knowledge of the structure-activity relationship between the GAG (or GAGs) wishing to be mimicked and/or congeners and/or structural information about ligand-receptor complexes (e.g., from X-ray crystallography, NMR) may influence the choice of linker. Generally the linker does not interact with the GAG receptor.

Preferred conjugates may be represented by the following formulae:

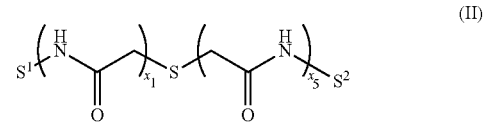

wherein $S^1$ and $S^2$ each independently represent anionic oligosaccharides, $x_1$ represents an integer from 1 to 4, and $x_5$ represents an integer from 1 to 4;

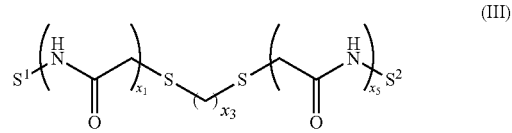

wherein $S^1$ and $S^2$ each independently represent anionic oligosaccharides, $x_1$ represents an integer from 1 to 4, $x_3$ represents 0 or an integer from 1 to 10, and $x_5$ represents an integer from 1 to 4; and (IV)

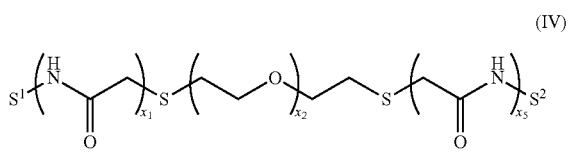

wherein $S^1$ and $S^2$ each independently represent anionic oligosaccharides, $x_1$ represents an integer from 1 to 4, $x_2$ represents 0 or an integer from 1 to 11, and $x_5$ represents an integer from 1 to 4.

Especially preferred anionic conjugates of the present invention may be represented by the following formula:

(V)

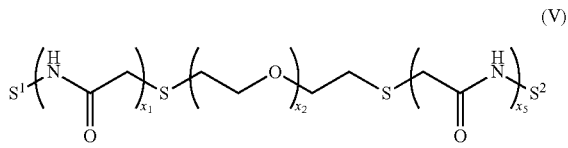

wherein $S^1$ and $S^2$ each independently represent anionic oligosaccharides, $x_1$ and $x_5$ equal 2 and $x_2$ represents 0 or an integer from 1 to 4.

In one aspect the present invention provides a process for preparing an anionic oligosaccharide of formula (I):

(I)

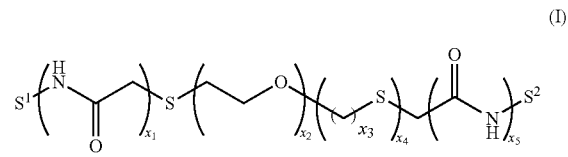

wherein:
- $S^1$ and $S^2$ each independently represent anionic oligosaccharides;
- $x_1$ represents an integer from 1 to 4;
- $x_2$ represents an integer from 0 to 11;
- $x_3$ represents an integer from 0 to 10;
- $x_4$ represents 0 or 1; and
- $x_5$ represents an integer from 1 to 4, the process comprising the steps of:
a) transforming each of the oligosaccharides into anionic oligosaccharides; and
b) conjugating the oligosaccharides;
wherein steps a) and b) may be performed in either order.

Methods for the transformation of an oligosaccharide into an anionic oligosaccharide through the sulfation and/or phosphorylation of one or more hydroxyl groups are known in the art, including methods for the selective sulfation of either primary hydroxyls or secondary hydroxyls or amino groups or combinations thereof. Such sulfation and/or phosphorylation may be of all of the free hydroxyl groups or may be partial sulfation and/or phosphorylation of the free hydroxyl groups.

Whilst the invention contemplates transforming each of the oligosaccharides into anionic oligosaccharides before and/or after preparing the conjugate, it is preferable to do so before formation of the conjugate. One reason for such a preference is to assist with controlling the homogeneity of the final product.

Without wishing to be bound by theory, it is believed that by coupling smaller anionic molecules together to form larger anionic molecules, greater control over the products and the degree of homogeneity is achieved. For example, the sulfation of small oligosaccharides (disaccharides to tetrasaccharides), containing 3 "sulfatable" groups per residue, proceeds to completion. On the other hand, sulfation of larger oligosaccharides is a more difficult process, and typically a heterogeneous mixture of undersulfated species is obtained. It is believed that in the larger systems, the extent of heterogeneity appears to be related to the number, or density, of sulfate groups—the more "sulfatable" groups that are present, the more heterogeneous the mixture. As an example, of the two pentasaccharides, Arixtra® and sulfomaltopentaose, the former contains 8 sulfate groups and is readily obtained in pure form, whereas the maltopentaose, which has 16 sulfatable groups, is obtained as a mixture. Furthermore, in the sulfation of the nonasaccharide Trestatin A, the average degree of sulfation obtained is 2.4 of a possible 3 per sub-unit (ignoring the reducing terminus), which equates to approximately 22 sulfate groups/molecule. Assuming sulfation is a stochastic event, and using the Poisson distribution to calculate the distribution of molecules with the designated number of sulfates, it would appear that the mixture contains molecules with between 14 and 27 sulfate groups. Moreover, except for the per-sulfated molecule, there are a very large number of possible isomers for each sulfated species—for example the number of isomers for the species containing 22 sulfate groups is 81,000. As can be seen, the sulfation of oligosaccharides of even modest length (nonasaccharide) can generate complex mixtures.

On the other hand sulfation of a trisaccharide, which may contain a total of 9 "sulfatable" groups, produces a mixture being 98% pure with respect to the persulfated trisaccharide. Coupling two such sulfated trisaccharides together produces a persulfated neo-hexasaccharide (18 sulfate groups) with a purity of 96%. Furthermore, the number of possible isomers for the undersulfated species is also reduced.

Scheme 1 shows examples of different synthetic routes (Paths A, B and C) that may be taken to synthesise the anionic oligosaccharide conjugates of the present invention. The substitution pattern on the depicted representative hexose ring of the oligosaccharide has been omitted for the sake of clarity. The skilled worker will appreciate that the protonated sulfate groups shown in structures 6 to 11 represent examples of anionic oligosaccharides as the expression is used herein owing to the ability of the functional groups to readily deprotonate, for example in water at pH of 5. As outlined above, the transformation of the oligosaccharides into anionic oligosaccharides may occur before or after conjugation of the oligosaccharides. In this respect, Scheme 1 shows examples of preferred synthetic strategies wherein sulfation of the oligosaccharides occurs prior to conjugation.

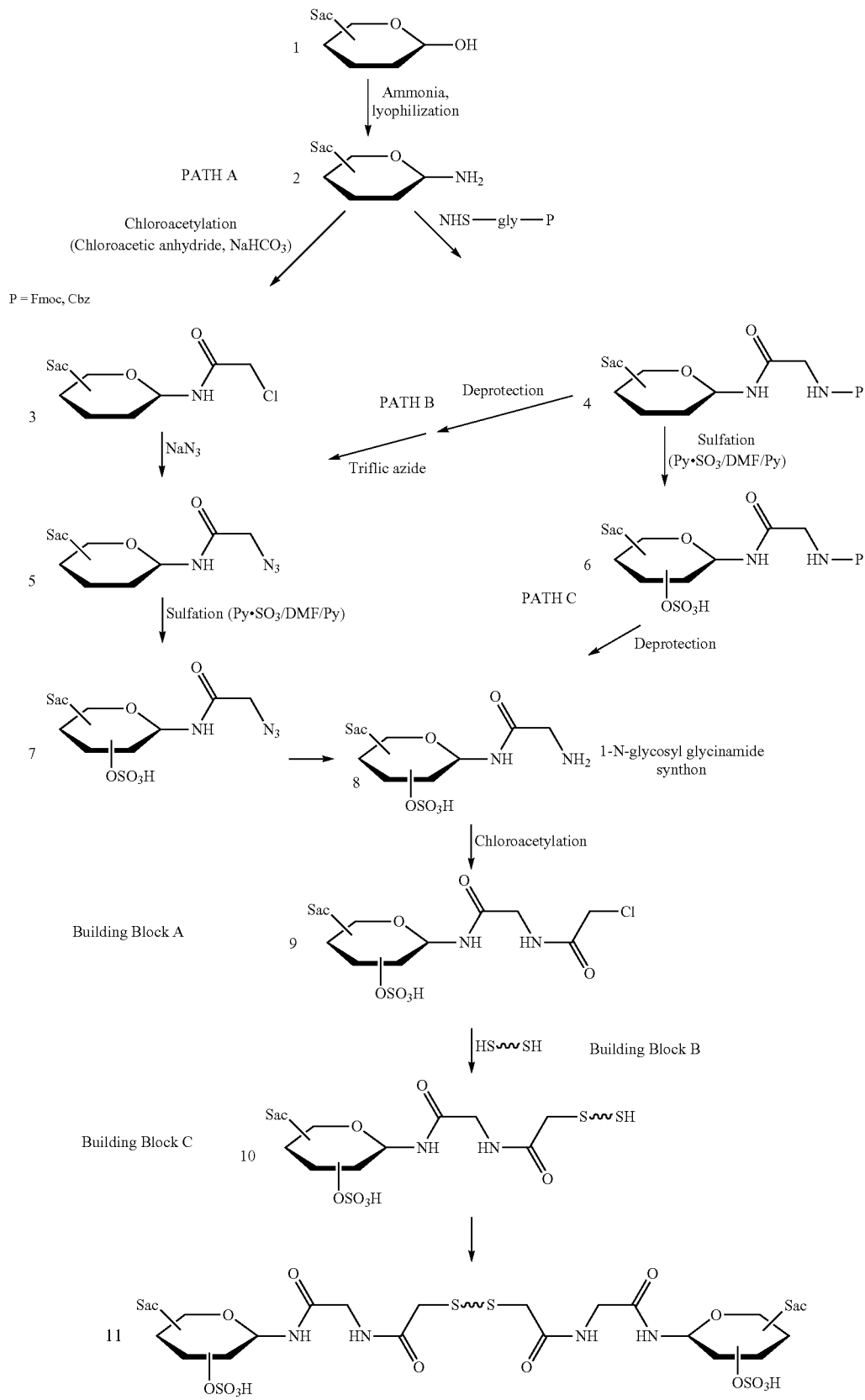

The step of conjugating the oligosaccharides may be achieved using the approach shown in Scheme 1. Typically oligosaccharides will be chosen that have a free reducing terminus. Conjugation through the reducing terminus of each of the oligosaccharides may occur after initial amination of the reducing terminus of each of the oligosaccharides. Through reaction of the amine group of the so-produced glycosylamine with one or more glycine-based moieties, it is possible to provide a reactive intermediate of structure 9, for example, for coupling to another such functionalised oligosaccharide. Two useful glycine-based moieties are N-protected (eg Fmoc) glycine and 2-haloacetyl compounds such as 2-chloroacetyl chloride or 2-bromoacetyl chloride. The coupling of the two derivatised oligosaccharide moieties occurs through a linker comprising at least one sulfur atom. In Scheme 1, Building Block B represents a dithiol compound. It is understood, however, that such a linker is representative only and does not exclude conjugates of formula (II) from the scope of the present invention. Specific examples of the dithiol of Building Block B, which may be commercially available, are given below together with identifiers for use within the specification:

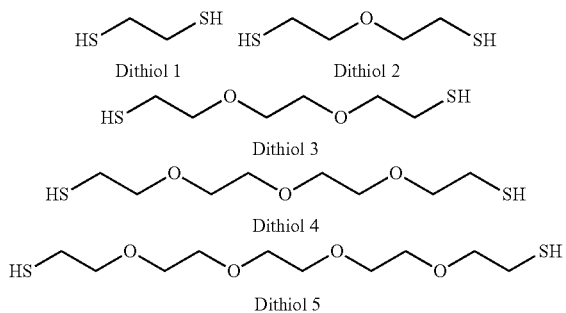

As used herein, the term "conjugate" takes its standard meaning and specifically refers to the covalent coupling of two oligosaccharides. It will be understood that in the structures referred to herein (such as formula (I)) the anionic oligosaccharides $S^1$ and $S^2$ are covalently bonded to the remainder of the conjugate. Accordingly it will be appreciated that $S^1$ and $S^2$ are monovalent residues of anionic oligosaccharides. The skilled worker will recognise that such coupling typically occurs as the result of the loss of part of each of the oligosaccharides when considered in isolation. For example, the amination reaction depicted in Scheme 1 that transforms oligosaccharide compound 1 into amine compound 2 occurs with loss of the hydroxyl group from compound 1. Nonetheless the skilled worker will routinely identify the hexose oligosaccharide portions of the anionic oligosaccharide conjugate of compound 11 in Scheme 1. Likewise the skilled worker will be able to routinely identify the anionic oligosaccharide portions denoted by $S^1$ and $S^2$ in formula (I):

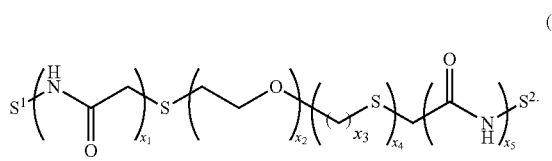

In other words, $S^1$ and $S^2$ may represent those residual portions of each of the anionic oligosaccharides that do not form part of the linker.

It has been found that the linkers of the present invention provide a facile approach to the synthesis of complex anionic oligosaccharide conjugates. In particular, the linkers provide the skilled worker with ready access to a series of anionic oligosaccharide conjugates which have differing lengths and hydrophilicities. Without wishing to be bound by theory it is believed that the use of thio functionality (such as in the dithiol compounds depicted above) allows the conjugation of complex anionic oligosaccharide conjugates without undesirable side-reactions occurring. The ease with which the conjugates may be synthesised allows the skilled worker to investigate the role that linker properties may play in the mimicry of GAGs by the anionic oligosaccharide conjugates of the present invention.

The typically convergent nature of the synthesis of the anionic oligosaccharide conjugates of the present invention provides the skilled worker with the ability to create libraries of structurally diverse compounds with relative ease. Degrees of structural diversity may be introduced through choice of each of the anionic oligosaccharides $S^1$ and $S^2$ of formula (I) (which may be the same or different), as well as the length and form of the linker moiety. In some embodiments, the synthetic precursors to such components may be prepared in isolation and introduced in a combinatorial approach. For example using as few as 3 anionic oligosaccharides and 3 linker moieties, the skilled worker is able to readily produce as many as 27 different anionic oligosaccharide conjugates.

The present invention provides processes for preparing large numbers of structurally diverse anionic conjugates which may form the basis for libraries of GAG mimetics. The anionic conjugates may have applications in the treatment of diseases that involve interaction between GAGs and one or more ligands. The anionic oligosaccharide conjugates of the present invention are useful in the treatment inflammatory respiratory disorders including anaphylaxis, asthma, allergic respiratory disease, allergic rhinitis, subepithelial fibrosis in airway hyperresponsiveness, chronic sinusitis, perennial allergic rhinitis, allergic bronchopulmonary aspergillosis in cystic fibrosis patients, COPD, ARDS/ALI, eosinophilic bronchitis, brochiectasis, bronchospasm, bronchial constriction, bronchial hyperreactivity, bronchial hypertrophy and bronchial inflammation. As used herein, the term "bronchial spasm" means an involuntary spasm of the breathing tubes of a patient. Bronchial constriction is both a term and a medical condition which is interchangeable with "bronchial spasm" in its use with respect to the purposes of this application. As used herein, the term "bronchial inflammation" refers to an inflammation of the breathing tubes of a patient. In addition, allergic syndromes, for example asthma, may be initiated by common cold viruses, especially the rhinovirus and the compounds disclosed can be used for treating infections in the upper respiratory passages, such as cold and flu and those from rhinovirus and coronaviruses. Bronchial constriction is also a symptom of anaphylaxis and the compounds disclosed may be used for treating anaphylaxis.

Anaphylaxis is a serious, rapid-onset, allergic reaction that can cause death. Life-threatening upper airway obstruction, bronchospasm and/or hypotension characterises severe anaphylaxis. There are about 100,000 episodes each year in the USA, of which approximately 1% result in death and about 66% are new cases. In most cases a specific trigger can be described but about 20% of cases are designated as idiopathic. Epinephrine has been accepted as the treatment of choice for many years, but it has been described as underutilised and not always effective (Golden, *Curr. Opin. Allergy Clin. Immunol.*, 7:331-336, 2007). The physicians' preference is for treatment with corticosteroids and anti-histamines despite little evidence for their efficacy during acute disease. Anti-histamines may help with histamine-mediated pathology, but not with effects arising from other mediators and may have limited efficacy in preventing ongoing mast cell and basophil activation. Like anti-histamines, corticosteroids have been suggested to play a role in disease management despite there being little clinical trial evidence for their efficacy, but their suggested use is on the basis that early administration of corticosteroids in patients with acute asthma is beneficial (El-Shanawany et al., *Clin. Exp. Immunol.* 153:1-9, 2008). Corticosteroids will not be effective during acute disease because their actions require protein synthesis and hence their activities are delayed.

Anaphylaxis involves the activation of mast cells and/basophils. It is most commonly triggered by exposure to insect venoms, foods, medications and allergen immunotherapy injections through a mechanism involving IgE and the high affinity receptor for IgE on mast cells and basophils. IgE synthesised in response to allergen exposure becomes fixed to IgE receptors (FcεRI) on the surface of mast cells and basophils. Receptor aggregation by IgE causes cell activation, pre-formed mediator release (including histamine, tryptases (including β-tryptase), carboxypeptidase A, TNF-α and chymase) and triggering of the immediate hypersensitivity response. Preformed granule mediators are released by exocytosis within minutes. Synthesis of arachidonic acid metabolites including prostaglandins and leukotrienes, and platelet activating factor (PAF) similarly occurs in minutes, whereas synthesis and release of inflammatory cytokines and chemokines may take hours and these mediators contribute to the late phase of a biphasic anaphylactic reaction. The cytokines and chemokines released include IL-5, IL-4, IL-13, granulocyte (G) colony stimulating factor (CSF), macrophage (M)-CSF, GM-CSF, IL-1β, IL-3, IL-6, IL-8, IL-10, IL-16, IL-18 and IL-22. Generally these mediators cause the recruitment and activation of additional cells including basophils, eosinophils and Th2 cells (Ogawa and Grant, *Immunol. Allergy Clin. N. Am.*, 27:249-260, 2007). In some patients described as having idiopathic anaphylaxis, FcεRI receptors may be aggregated through autoimmune mechanisms in the absence of IgE (Simons, *J. Allergy Clin. Immunol.* 121:S402-7, 2008) and there is some evidence of an alternative pathway involving IgG and the IgG receptor. This latter pathway does not trigger histamine release; rather PAF is the main early mediator (Peavy and Metcalfe, *Curr. Opin. Allergy Clin. Immunol.*, 8:310-314, 2008).

In the early phase of anaphylaxis histamine stimulates vasodilation and increases vascular permeability, heart rate, cardiac contraction and glandular secretion. Prostaglandin D2 is a bronchoconstrictor, pulmonary and coronary vasoconstrictor, and a peripheral vasodilator. Leukotrienes also promote bronchoconstriction and increased vascular permeability, as well as promoting airway remodelling. PAF similarly causes bronchoconstriction and increased vascular permeability. TNF-α activates neutrophils; recruits other effector cells, and enhances chemokine synthesis, which leads to further inflammatory cell recruitment. These overlapping and synergistic effects contribute to the overall pathophysiology of anaphylaxis that variably presents with generalized urticaria and angioedema, bronchospasm, and other respiratory symptoms, hypotension, cardiovascular symptoms (including fainting), and nausea as well as other gastrointestinal symptoms (Peavy and Metcalfe, *Curr. Opin. Allergy Clin. Immunol.*, 8:310-314, 2008). IL-4 is a key cytokine in the late phase of anaphylaxis and as well as stimulating and maintaining Th2 cell proliferation and switching B cells towards IgE synthesis, the most rapid and dramatic effect of this cytokine on anaphylaxis is to markedly enhance the responsiveness of targeted cells to vasoactive mediators including histamine, serotonin, PAF and cysteinyl leukotrienes (Ogawa and Grant, *Immunol. Allergy Clin. N. Am.*, 27:249-260, 2007).

Asthma is characterized by inflammation of the air passages resulting in the temporary narrowing of the airways that transport air from the nose and mouth to the lungs. Asthma symptoms can be caused by allergens or irritants that are inhaled into the lungs, resulting in inflamed, clogged and constricted airways. Symptoms include difficulty breathing, wheezing, coughing, tightness in the chest. In severe cases, asthma can be deadly. Asthma is probably not a single disease, but rather a complex of multiple, separate syndromes that overlap. The following classification is based on the reports of Wenzel. *Lancet;* 368:804-813, 2006, and Green et al. *Curr. Opin. Allergy Immunol.* 7:43-50, 2007.

Allergic asthma: this is the largest asthma phenotype. This is especially true in childhood asthma but probably also in a high proportion of adults with asthma. Individuals presenting with this phenotype usually experience their first symptoms in childhood, but it can present at any age. Family history of asthma and early exposure to allergens are important in the initiation of allergic asthma. In addition to the standard therapies, targeted therapies: immunotherapy or monoclonal antibodies against IgE, have been used successfully. However, not all people with allergic asthma respond to anti-IgE-therapy.

Occupational asthma: up to 15% of adult onset asthma falls in this group. It has the following subphenotypes: (1) development of an immunologically mediated response to the causal agent, usually a high molecular weight agent—has similarities to allergic asthma through development of IgE antibodies; (2) development of an immunologically mediated response to low or high molecular weight triggers and an IgE response is not consistently seen; (3) development of a non-immunological rapid on-set response after exposure to a high concentration of irritant chemicals.

The airway inflammation is similar in both immunological phenotypes and resembles that of allergic asthma e.g. presence of eosinophils, lymphocytes, mast cells and the thickening of the reticular basement membrane. By contrast the asthma caused by irritant chemicals is quite different and is characterized by fibrosis of the bronchial wall and epithelial denudation and fibrinohaemorrhagic exudates in the submucosa without eosinophilic inflammation. The immunological types of this asthma can continue in the absence of exposure to the causal agent.

Aspirin-induced asthma: aspirin and other non-steroidal anti-inflammatory drugs are the triggers. It is common in the severe asthma population and is associated with little evidence of atopy, raised leukotrienes and high numbers of eosinophils in both tissue and blood. There is severe rhinosinusitis and nasal polyps and adult onset. This phenotype is poorly responsive to corticosteroids.

Menses-related asthma: this is not well characterised. It probably only occurs in a small proportion of women but it can be severe.

Exercise-induced asthma: the mechanisms that trigger this asthma seem to involve acute inflammatory cell (usually mast cell), epithelial and vasoactive responses but the pathogenesis is unclear. Whether exercise-induced asthma represents the development of bronchoconstriction in response to exercise in all asthmatics or whether it occurs in only some is unclear.

Although inflammation is a hallmark of asthma, not all asthma phenotypes have predominately eosinophilic inflammation, although this is the most common and the best studied.

Eosinophilic asthma: studies have defined an eosinophilic phenotype by sputum or biopsy testing in patients with varying degrees of asthma severity and have demonstrated consistently around 50% of asthmatics have this phenotype. Other studies have suggested that eosinophilic inflammation may be present in a higher proportion of patients than that detected using sputum or biopsy testing. In one study 50% of the patients with severe asthma thought to be non-eosinophilic actually had eosinophilic inflammation, but in the distal lung.

Neutrophilic asthma: seen most commonly in patients with severe disease. Many patients with neutrophilic inflammation can have concomitant eosinophilic inflammation in tissue biopsies whereas the sputum assessment may show a clear predominance of neutrophils. The association of neutrophils with severe asthma could be caused by treatment with high dose steroids, which have been shown to decrease neutrophil apoptosis in vitro. Neutrophilic asthma was associated with increases in IL-8 and neutrophil elastase. Approximately 20% of patients had neutrophilic asthma and a further 8% had both eosinophilic and neutrophilic inflammation (from a study of 93 patients).

Paucigranulocytic asthma: patients with sputum cell counts in the normal range (~30% of the 93 patients had this subphenotype).

Allergic rhinitis is an allergen-induced upper-airway disease, characterized by hyperreactive airway mucosa and episodes of symptom chronicity with periods of acute exacerbation. Allergic individuals become sensitized to and may develop IgE antibodies against allergens such as pollens, dust mites, animal dander and mould spores. The immediate allergic response to antigen is termed the early phase response. The mediators released during this phase are histamine, kinins, neutral proteases and a variety of cytokines. Activation of mast cells leads to the production of leukotrienes and prostaglandins and together these mediators give rise to the watery rhinorrhoea, sneezing and itching within minutes of allergen exposure. This is followed several hours later by the late-phase response involving infiltration of inflammatory cells and the release of mediators into the nasal mucosa. Symptoms are similar to that of the early phase response but congestion predominates (Walls et al, *Med. J. Aust.;* 182:28-33, 2005). Allergic rhinitis has been subdivided into "intermittent" and "persistent" disease. Intermittent disease describes a condition whereby symptoms are present less than 4 days per week, or less than 4 weeks at a time. Persistent disease means that symptoms are present for more than 4 days per week and more than 4 week at a time (Pawanker, *Curr. Opin. Allergy Clin. Immunol.;* 4:1-4, 2004.)

Allergic rhinitis and allergic asthma are diseases that involve an inflammatory response. They have similar underlying etiology and the key cytokines for each disease are the Th2 subset of T-cell cytokines IL-5, IL-4 and IL-13 and GM-CSF. These diseases are characterized by a marked inflammatory cell infiltrate comprising eosinophils, mast cells, T-lymphocytes and cells of the monocytic lineage. The adhesion molecules, P-selectin, MAC-1 and PECAM-1 play an important role in the extravasation of leukocytes and are likely to be involved in the inflammatory process. Further, the eotaxin family of chemokines plays a key role in these diseases as they are the prime chemotactic factors stimulating eosinophil and CD4+ T lymphocyte infiltration.

Recently IL-17 family cytokines (in particular IL-25 (IL-17E)) have been described as initiating or amplifying allergic inflammation. Of particular interest are IL-17 (IL-17A) and IL-25. In vivo studies suggest that IL-25 may play a pivotal role in the development of Th2 mediated allergic inflammation. Transgenic mouse studies where the effects on allergic reactions of enforced expression of IL-25 in the airways were examined indicated that the IL-25 enhanced Th-2 cell-mediated allergic inflammation. In addition, administration of IL-25 by intra-tracheal instillation resulted in both airway hyperreactivity with mucus hypersecretion, and eosinophilic inflammation in the lung tissue, processes that required respectively IL-13 and IL-13 signalling, and IL-5/eotaxin (Tamachi et al., *J. Allergy Clin. Immunol.* 118:606-614, 2006; Sharkhuu et al., *Clin. Exp. Allergy* 36:1575-1583, 2006). Data obtained with an IL-25 blocking antibody indicate that IL-25 is critical for the development of airway hyperreactivity. Blocking IL-25 activity significantly reduced levels of IL-5, IL-13 and IgE secretion, eosinophil infiltration and goblet cell hyperplasia in allergic asthma (Ballantyne, *J. Allergy Clin. Immunol.* 120:1324-1331, 2007).

In other work using a mouse model of asthma IL-17 was found to be produced primarily by alveolar macrophages, and expression was up-regulated by mast cell released mediators (Song et al., *J. Immunol.* 181:6117-6124, 2008). In asthma patients IL-17 expression was increased in the lungs, sputum, BAL fluid or sera and the severity of airway hyperreactivity correlated with IL-17 levels (Wang and Liu, *Curr. Opin. Immunol.* 20:697-702, 2008). However, the effects of IL-17 seem to be primarily on neutrophil levels as over expression of IL-17 or the administration of IL-17 into the lungs results in a neutrophil influx associated with elevated levels of chemokines that act on neutrophils. There is good evidence that neutrophil levels contribute to bronchoconstriction, non-specific AHR, hypersecretion of mucus proteins and lung tissue damage, particularly in severe asthma (Linden et al., *Eur. Respir. J.* 25:159-172, 2005).

The 3-D structure of only one IL-17 family member has been solved. This revealed IL-17F is a structural homologue of the cysteine knot family of proteins and dimerises similarly to members of the nerve growth factor (NGF) family. The core of the IL-17F monomer comprises two pairs of anti-parallel β-strands (pair 1: strands 1&2; Pair 2: strands 3&4). Two disulfide bridges connect strands 2 and 4, and a third disulfide connects the loop between strands 3 and 4 of one protomer to the N-terminal extension of the adjacent monomer. Based on an amino acid sequence alignment the cysteine knot fold and the location of the β-strands are believed to be preserved in all IL-17 family members. IL-17, in particular, should resemble IL-17F in structure, whereas IL-25 (IL-17E) may have its N-termini in a different conformation (Hymowitz et al., *EMBO J.* 20:5332-5341, 2001). An examination of the IL-17F structure, coloured according to the electrostatic surface potential, reveals a protein displaying many basic surface residues orientated so that glycosaminoglycan binding is a possibility. A comparison of the amino acid sequences of IL-17F, IL-17 and IL-25 indicate overall conservation of basic residues, but with IL-25 being more basic that the other two proteins. Thus, an anionic oligosaccharide conjugate binds these cytokines, with IL-25 binding with the highest affinity. The location of the receptor binding sites on IL-17, IL-17F and IL-25 has not been determined. However, a striking feature of the structure of IL-17F is a large cavity in the area of the dimer interface. Hymowitz et al *EMBO J.* 20:5332-

5341, 2001 believe the amino acids making up this region display characteristics expected of a pocket that may bind another protein (possibly a receptor domain) and from an analysis of the amino acid sequence this pocket should be conserved across all family members including IL-25. This potential receptor binding pocket abuts on a line of basic residue clusters that is indicative of an anionic oligosaccharide conjugate binding region. As anionic oligosaccharide conjugate binding interferes with IL-17 and IL-25 binding their receptors it is likely this line of basic residues abutting the receptor binding pocket is the site where the anionic conjugate binds IL-17 and IL-25.

There is a growing realization that asthma and allergic rhinitis are components of a single inflammatory airway disease. This conclusion is supported by epidemiological data showing that more than 80% of persons with allergic asthma have allergic rhinitis, and that up to 50% of patients with allergic rhinitis have asthma (Gelfand, *J. Allergy Clin. Immunol,* 114:S135-138, 2004; Passalacqua et al, *Curr. Opin. Allergy Clin. Immunol.* 4:177-183, 2004). Moreover, longitudinal and follow-up studies have shown that rhinitis usually precedes asthma and is a risk factor for asthma. Allergic Rhinitis increases the risk of developing asthma by at least three-fold and correct treatment of allergic rhinitis with intranasal steroids has a favourable effect on bronchial symptoms, significantly reducing the rate of hospital admittance and emergency department visits for asthma exacerbation (Passalacqua et al., *Curr. Opin. Allergy Clin. Immunol.* 4:177-183, 2004). These diseases are a complex mixture of pathologies, involving at least the various cytokines, chemokines and cell adhesion molecules indicated above.

Mast cells and histamines play an important role during the initial allergic rhinitis response. However, as allergic rhinitis progresses the role of histamines diminishes, making anti-histamines less effective as a therapy (Gelfand, *J. Allergy Clin. Immunol* 114: S135-138, 2004). During the initial allergic rhinitis response sensitized mast cells degranulate within minutes of allergen exposure releasing preformed and newly synthesized mediators including histamine, proteases, cysteinyl leukotrienes, prostaglandins and cytokines. Allergic rhinitis progression is dependent upon mediators associated with the infiltration of eosinophils, basophils, neutrophils, mononuclear cells and T-lymphocytes (Gelfand, J. *Allergy Clin. Immunol,* 114:S135-138, 2004; Passalacqua et al, *Curr. Opin. Allergy Clin. Immunol.* 4:177-183, 2004). The association of eosinophils and IL-5 with allergic rhinitis has been appreciated for some time. Repeated studies have found increased levels of Th2-type cytokines including IL-5 and IL-4, and increased amounts of eosinophil cationic protein (ECP), a marker of activated eosinophils, following provocation with allergen (Blaiss, *Allergy Asthma Proc.* 26: 35-40, 2005. The influx of eosinophils correlates closely with the development of symptoms. In addition the loss of epithelial integrity in the nasal mucosa of rhinitis patients correlates with eosinophil numbers rather than the numbers of mast cells or neutrophils (Borish, *J. Allergy Clin Immunol.* 112: 1021-1031, 2003). It seems allergic rhinitis evolves from an acute, primarily mast cell-mediated process that is responsive to anti-histamines, through to a chronic inflammatory disease that is primarily eosinophil-mediated and is much less responsive to anti-histamines. This is the case for patients with persistent allergic rhinitis. Progression to a condition that is refractory to anti-histamines can also occur within an allergy season, for seasonal suffers. For other patients with mild intermittent disease antihistamines do remain an effective therapy, reflecting intermittent allergen exposures, which are not of sufficient duration to drive disease progression into the anti-histamine-resistant phase.

The first line treatment for asthma is inhaled corticosteroids (ICS), which are usually used in combination with $\beta_2$-agonists (Barnes, *Br. J. Pharmacol.* 147 Suppl 1:S297-303, 2006). $\beta_2$-agonists relieve the symptoms rather than treat the underlying inflammation and have the potential to make asthma worse if used frequently in the absence of ICSs. Nevertheless, this seems to be the therapy preferred (despite its side-effects) because of the immediacy of its effect. $\beta_2$-agonist therapy in the absence of ICS has been given a "black box" listing by the FDA because of the potential cardiac problems associated with this therapy. Although side effects are lower than with oral formulations, ICS are not without adverse local and systemic side effects. A side effect of corticosteroids is the suppression of the hypothalamic-pituitary-adrenal axis (HPAA): clinically relevant adverse effects are seen and this is more apparent with some medications than others. Bone density and fractures can also be a problem: certain effects of ICS on bone metabolism are detectable but the clinical relevance is unclear. Finally growth retardation in children is another issue that may worry patients (Allen, *Adv Pediatr.* 53:101-110, 2006). On balance the side effects are acceptable given the severe complications of sustained/uncontrolled asthma.

Other therapies for asthma include:

(1) Omalizumab, an anti-IgE antibody (Genetech) is viewed as not cost effective for standard asthma treatment. It is primarily used as add-on therapy to ICS because it does not improve airway responsiveness and has modest efficacy. The dose constraints and delivery mechanism (subcutaneous injection) are an added disadvantage. Moreover, a warning from the US Food and Drug Administration (FDA) has linked omalizumab injection to life-threatening anaphylaxis and more worrying in some patients this anaphylaxis is delayed occurring more than 2 hours after injection to more than 24 hours after injection.

(2) Anti-leukotrienes (anti-LTs), which can cause bronchodilation. Their effect is additive to that of short-acting $\beta_2$-receptor agonists although alone they have a relatively modest effect. Anti-LTs primarily affect the early asthmatic response (EAR) whereas, ICS show pronounced effects on late asthmatic responses (Palmqvist et al, *Allergy* 60:65, 2005). For these reasons anti-LTs have been trialed in combination with ICS. Anti-leukotrienes are not cost effective. They have virtually no side effects, but their efficacy is low.

The usual therapies for allergic rhinitis are anti-histamines or intranasal corticosteroids (Neilsen and Dahl, *Am. J. Respir. Med.* 2:55-65, 2003; Yanez and Rodrigo, *Ann. Allergy Asthma Immunol.* 89:479-84, 2002). The older first generation oral H1 antagonists (anti-histamines) have a number of adverse side-effects, the best recognized being drowsiness and anti-cholinergic effects. The second generation drugs were developed to overcome these effects. However, recent studies have indicated that the division between first and second generation H1 antagonists in terms of drowsiness is not clear cut (Golightly and Greos, *Drugs* 65:341-84, 2005). Labels for Cetirizine, the most potent anti-histamine approved by the FDA, include a warning about the possible adverse effect of somnolence and caution with driving and use of heavy equipment when taking the drug was urged. In addition, concurrent use of alcohol or other central nervous system (CNS) suppressants should be avoided because additional reduction in alertness and CNS performance may occur. Moreover, anti-histamines are not effective against the congestion associated with chronic allergic rhinitis. Allergic rhinitis progresses to a disease that is primarily eosinophil mediated and refractory to anti-histamine therapy. When this happens intranasal corticosteroids (INCS) are the main therapy. Indeed, for many clinicians INCS are the drugs of choice for treatment of all allergic rhinitis as the corticosteroid acts to reduce eosinophil inflammation. Although INCS are generally considered safe the recommendation is to reduce steroid dose as much as possible and to optimize steroid-sparing strategies (Skoner, *Curr. Opin. Allergy Clin. Immunol.* 2:7-10, 2002).

The underlying etiology of chronic obstructive pulmonary disease (COPD) is different from that of allergic inflammatory diseases (Sutherland and Martin, *J. Allergy Clin. Immunol.* 112:819-27, 2003). COPD involves a chronic inflammatory process affecting peripheral airways and lung parenchyma and inflammation is worse during exacerbations. A major contributory factor to the development of COPD is the inflammatory response to cigarette smoke. The pathological indicators of COPD are destruction of the lung parenchyma (pulmonary emphysema), inflammation of the small peripheral airways (respiratory bronchitis) and inflammation of the central airways. Most patients with COPD have all three pathological conditions (chronic obstructive bronchitis, emphysema and mucus plugging) that exhibit different patterns of inflammation (Adcock and Ito, *Proc. Am. Thorac. Soc.* 2:313-319, 2005). Neutrophils and macrophages are considered to be the main effectors of disease. Analyses of sputum and bronchoalveolar lavage fluid show increases in both neutrophils and macrophages in these secretions from COPD patients. In addition, there is increasing evidence that a significant sub-group of COPD patients exist who have chronic airway eosinophilia.

Alveolar macrophages play a key role in COPD. They are localized to sites of alveolar destruction, and their numbers are positively correlated with disease severity, airway obstruction and degree of alveolar wall damage in emphysema. Airway tissue neutrophils are increased in the large and small airways of COPD patients during exacerbations and in severe COPD, or during infections. Patients with COPD also display either an increase in the CD8+/CD4+ T cell ratio, or an increase in the total numbers of both CD8+ and CD4+ T cells in the airway wall (MacNee, *Proc. Am. Thorac. Soc.* 2:258-266, 2005). The bronchioles are obstructed by fibrosis and infiltrated with macrophages and T lymphocytes.

There are three morphological forms of COPD: chronic bronchitis, obstructive bronchiolitis and emphysema (Szilasi et al., 2006. *Pathol. Oncol. Res.* 12:52-60). The inflammation associated with chronic bronchitis is located in the epithelium of the central airways. The inflammatory process is associated with increased production of mucus and defective mucociliary clearance. Inflammation is observed in the mucosa, in the smooth muscle layers and submucosal glands. In large airways mononuclear cell, macrophage, CD8+ T cells and plasma cell involvement is common in stable COPD and during exacerbations of chronic bronchitis. CD8+ T cells release tumor necrosis factor-α (TNF-α), a potent proinflammatory mediator. The role of the neutrophil is not clear. Neutrophils are seen in the large airways only during exacerbations and in severe COPD. They are however, observed early on in the airway lumen and in the sputum.

Obstructive bronchiolitis or small airway obstruction is an inflammatory condition that involves the small and peripheral airways. The typical feature is collapsed lumen with increased mucus. Macrophages and CD8+ T cells dominate small airway inflammation, although the inflammatory changes showed a positive correlation with airflow obstruction in COPD. For example, in mild to moderate stable COPD macrophages were dominant, while in severe disease neutrophils were the predominant inflammatory component, whilst during mild exacerbations eosinophils are found. Increased numbers of fibrobalsts and myofibroblasts and enhanced extracellular matrix is found in the subepithelium of the small airways in obstructive bronchiolitis. This pathology suggests a mechanism of repetitive injury and healing that leads to fibrosis and scar tissue. The net result is airway narrowing.

Emphysema is defined by permanent air space enlargement caused by destruction and enlargement of lung tissue beyond the terminal bronchiole. The mechanism of the disease involves unregulated inflammation and the release of large amounts of proteolytic enzymes. Protease/antiprotease imbalance is the presumed cause for pulmonary emphysema. Although inflammation is dominated by CD8+ T cells, macrophages and neutrophils produce excessive amounts of proteases including leukocyte elastase, cathepsin G, proteinase 3, matrix metalloprotineases (MMPs), cysteine proteinases and plasminogen activator. These enzymes destroy the elastin and other components of the alveolar wall with elastase being the enzyme most heavily implicated in this process.

The proinflammatory mediators of these disease processes include leukotriene-B4, IL-8 and other chemokines (e.g. MIP-1α, MCP-1), TNF-α, IL-13 and IL-4 (Barnes, *Pharmacol. Rev.* 56:515-548, 2004). It has been suggested that the inhibitory effects of TNF-α and IL-4 on the production of the regulatory cytokine TGF-β by bronchial epithelial cells may contribute to the progression of the inflammatory response. In addition, increased levels of IL-6, IL-1β, TNF-α, and IL-8 have been measured in sputum with further increases during exacerbations.

COPD is a very significant burden on society. It is the fifth leading cause of death in the UK. It affects 5% of the adult population and is the only major cause of death in the US in which morbidity and mortality are increasing. By 2020 it is estimated that COPD will be the $3^{rd}$-leading cause of death and the $5^{th}$-leading cause of disability worldwide (Halpin and Miravitlles, *Proc. Am. Thorac. Soc.* 3:619-623, 2006). Existing therapies for COPD are grossly inadequate. None slow disease progression and response to treatments is poor. COPD is relatively resistant to the anti-inflammatory effects of corticosteroids. Nevertheless current pharmacologic options include drugs to assist in stopping smoking, short and long-acting $\beta_2$-agonists, short and long acting anticholinergics, inhaled corticosteroids, theophylline, N-acetyl cysteine and other mucolytics and oxygen (Anzueto, *Am. J. Med.* 119:S46-S53, 2006; Barnes and Stockley, *Eur. Respir. J.* 25:1084-1106, 2005). The short and long-acting $\beta_2$-agonists were introduced to improve bronchodilation. They are often used in combination with anticholinergics because they produce bronchodilation via different pathways. Inhaled corticosteroids are often used in combination with $\beta_2$-agonists and improvements in exacerbation rates are greater than that seen with the individual component. Theophylline is a useful bronchodilator. The mode of action of N-acetyl cysteine is not clear but it may act as a mucolytic or antioxidant to improve cough symptoms and in some patients it appears to reduce exacerbation frequency.

Despite these therapies the only intervention clearly shown to reduce mortality in clinical trials is smoking cessation.

Acute lung injury (ALI) and acute respiratory distress syndrome (ARDS) are respiratory inflammatory conditions that are associated with high mortality rates. The pathogenesis of ALI and ARDS involve uncontrolled host defense responses that lead to inflammation, endothelial damage, enhanced coagulation, diminished fibrinolysis and fibroproliferation. ARDS is a clinical syndrome resulting from a variety of etiologies. In 1994 a definition of the disease was recommended by the American-European Consensus Conference on ARDS committee; the criteria include: (1) acute onset, (2) bilateral infiltrates on chest radiograph, (3) pulmonary artery wedge pressure≤18 mm Hg or the absence of clinical evidence of left atrial hypertension, and (4) Pao$_2$/Fio$_2$ ratio≤300 (defining ALI) or Pao$_2$/Fio$_2$ ratio≤200 (defining ADRS as a more severe form of ALI) (Cepkova and Matthay, *J. Intensive Care Med.*, 21:119-143, 2006). Diffuse alveolar damage is a characteristic of ARDS. Initiating events that lead to diffuse alveolar damage and subsequently to ALI or ARDS include pneumonia, aspiration, pulmonary emboli, near-drowning, inhalation injury, reperfusion pulmonary edema, trauma, surgery, burn injury, drug overdose, acute pancreatitis, cardiopulmonary bypass and massive blood transfusions, but overall sepsis is associated with the highest risk of developing ALI or ARDS. There are three overlapping phases of the disease: Exudative phase (in first 4-7 days), Proliferative phase (≥7-14 or 21 days) and Fibrotic phase (≥14 or 21 days) (MacLaren and Stringer, *Pharmacotherapy*, 27:860-873, 2007).

The initial early phase (exudative phase) is characterized by increased permeability of the endothelial and epithelial barriers of the lung, with accumulation of protein-rich and highly cellular edema fluid in the lung interstitium and alveoli. The edema fluid contains hyaline membranes and a variety of inflammatory cells but neutrophils predominate. Thus the pathological correlate termed: diffuse alveolar damage, consists of hyaline membranes plus at least one of the following: alveolar type I or endothelial cell necrosis, edema, interstitial fibrosis, or prominent alveolar cell type II proliferation. Some patients recover during the first week of the disease, others die during that phase, but some progress into a sub-acute phase of ALI/ARDS that develops 7 or so days after onset. During this sub-acute phase the alveolar space becomes filled with mesenchymal cells, their products and new blood vessels. There is evidence of interstitial and alveolar fibrosis with proliferation of type II cells and destruction of portions of microcirculation in the lungs. In some patients respiratory failure continues beyond 14 days, and this chronic phase is characterized by extensive pulmonary fibrosis with loss of normal alveolar architecture and the progressive development of emphysematous regions in the lung (Cepkova and Matthay, *J. Intensive Care Med.*, 21:119-143, 2006).

During the acute phase there is a marked accumulation of neutrophils. Neutrophils predominate in the pulmonary edema fluid and bronchoalveolar lavage fluid obtained from affected persons. Alveolar macrophages secrete cytokines e.g. interleukin (IL)-1, IL-6, IL-8, IL-10 and tumour necrosis factor (TNF)-α, which act locally to stimulate neutrophil chemotaxis and to activate neutrophils. Neutrophils then release oxidants, proteases (including neutrophil elastase), leukotrienes and other proinflammatory mediators (Ware and Matthay, *New England J. Med.* 342:1334-1349). These mediators interact in complex ways to injure and inflame the alveolar capillary interface. This heterogeneity of mediators may explain why anti-mediator therapies that appear promising in animal models have not translated into a beneficial clinical outcome when given in clinical trials. Treating ARDS with corticosteroids, ibuprofen, n-acetyl cysteine, lisofylline, prostaglandinE, anti-TNF-α antibody, IL-1 receptor antagonist and ketoconazole have all been disappointing in large clinical trials.

Identification and treatment of the inciting clinical disorder is an important aspect of managing ALI/ARDS. In many patients the insult that caused the injury cannot be treated except to prevent recurrence and in these patients optimal supportive care is paramount. The mainstay of supportive care is mechanical ventilation and recent trials have shown that, compared with a traditional approach to mechanical ventilation, a strategy aimed at delivering lower tidal volumes and limiting plateau pressure resulted in reduced mortality (Mortelliti and Manning, *Am. Family Physician* 65:1823-1830, 2002).

It has now been found that the anionic oligosaccharide conjugates of the present invention interact with a number of ligands which are responsible, in part or whole, for the conditions discussed above. Preferably the ligand is a peptide, polypeptide or protein although the present invention extends to the ligand being a carbohydrate, lipid, glycoprotein or a molecule obtained from natural product screening or from a chemical library. Suitable protein targets include those that have been described as GAG (heparin, heparin sulphate, chondroitin and hyaluronan) binding proteins. Examples of protein ligands include, but are not limited to: histamine, a cytokine including an interleukin (e.g. IL-1, IL-2, IL-3, IL-4, IL-5, IL-6, IL-7, IL-8, IL-9, IL-10, IL-11, IL-12, IL-13, IL-14, IL-15, and members of the IL-17 family including IL-25), interferon (e.g. α-interferon, β-interferon, γ-interferon) or a growth factor including but not limited to G-CSF, M-CSF, GM-CSF, BDNF, CNTF, EGF, EPO, FGF1, FGF2, FGF3, FGF4, FGF5, FGF6, FGF7, FGF8, FGF9, FGF10, FGF11, FGF12, FGF12, FGF13, FGF14, FGF15, FGF16, FGF17, FGF18, FGF19, FGF20, FGF21, FGF22, FGF23, LIF, MCP1, MCP2, MCP3, MCP4, MCP5, M-CSF, MIP1, MIP2, KC, NGF, NT 3, NT4, NT5, NT6, NT7, OSM, PBP, PBSF, PDGF, PECAM-1, PF4, RANTES, SCF, TGFα, TGFβ$_1$, TGFβ$_2$, TGFβ$_3$, TNFα, TNFβ, TPO, VEGF, GH, insulin and the like; an enzyme (e.g. superoxide dismutase, eosinophilic cationic protein, tryptases (including β-tryptase), chymases, elastases, phospholipase A2 or prostaglandin endoperoxide); chemokines such as eotaxin (eotaxin-1, -2 or -3); or a soluble or cell- or virus-bound receptor (e.g. inositol triphosphate receptor).

In one aspect the invention provides an assay or screen for determining the biological effect of one or more anionic oligosaccharide conjugates, the assay comprising the steps of:

a) contacting a ligand, cell or animal with one or more anionic oligosaccharide conjugates each independently having the following formula (I):

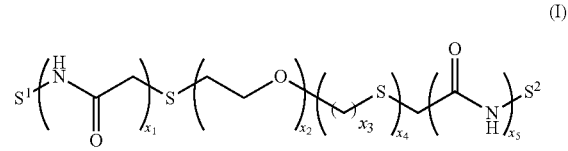

wherein:
S$^1$ and S$^2$ each independently represent anionic oligosaccharides;
x$_1$ represents an integer from 1 to 4;
x$_2$ represents an integer from 0 to 11;
x$_3$ represents an integer from 0 to 10;
x$_4$ represents 0 or 1; and
x$_5$ represents an integer from 1 to 4;
and b) quantifying an effect of the one or more anionic oligosaccharide conjugates on the ligand, cell or animal.

The interaction with a ligand may be detected by any convenient means such as gel retardation, filter retardation, affinity co-electrophoresis, bioluminescent resonance energy transfer (BRET) assays, fluoresence resonance energy transfer (FRET) assays, fluorescence polarisation (FP) assays, scintillation proximity assays or immobilization to biochips or other surfaces including those coupled with mass spectrometric detection.

The latter may be accomplished by first immobilizing the anionic oligosaccharide conjugate to a chip and then adding the ligand. Alternatively, the ligand may be immobilized to a chip and used to screen for the ability of an anionic oligosaccharide conjugate to bind thereto.

Yet another alternative is to immobilize a GAG, such as heparin, to a solid support and then screen for the ability of an anionic oligosaccharide conjugate to inhibit binding of a ligand to the immobilized heparin.

Accordingly, a particularly useful assay is to admix the ligand and the anionic oligosaccharide conjugate and screen for the ability of the anionic oligosaccharide conjugate to inhibit binding of the ligand to a GAG (e.g. heparin or heparan sulfate) bound to a chip.

Another aspect of the present invention contemplates, therefore, a method for producing a GAG mimetic that interacts with a ligand such as a protein, said method comprising producing a library of anionic oligosaccharide conjugates and then screening each member of said library for an ability to interact with said ligand or to inhibit the interaction between the ligand and Heparin-like GAGs (HLGAGs) known to interact with said ligand.

In a preferred embodiment, the anionic oligosaccharide conjugate binds a secreted cellular product which may be a protein and, in so doing, inhibits the interaction between the ligand and a GAG such as heparin.

There are, of course, any number of other assays, which may be used to screen for interaction between an anionic oligosaccharide conjugate and a ligand or used to screen for inhibition of interaction between a ligand and a GAG known to bind to the ligand. Another assay is a filter binding assay. In this assay, one of an anionic oligosaccharide conjugate, or a ligand is labelled with a reporter molecule capable of providing an identifiable signal such as a fluorescent dye and both molecules are allowed to interact in solution. The resulting mixture is then passed through a filter capable of retarding one of the anionic oligosaccharide conjugate or anionic oligosaccharide conjugate composite molecule or the ligand or only an anionic oligosaccharide conjugate-ligand complex or anionic oligosaccharide conjugate composite molecule-ligand complex.

In one embodiment, for example, the filter is a nitrocellulose filter which retards proteins. In this case, if the anionic oligosaccharide conjugate, labeled with a reporter molecule, fails to pass through the filter, then the presence of the reporter signal in the filter indicates binding of the anionic oligosaccharide conjugate to the protein.

In another embodiment, heparin or heparan sulfate is labeled with the reporter molecule and reacted with the protein in the presence of different anionic oligosaccharide conjugates. Passage of heparin or heparan sulfate through the filter is indicative of an anionic oligosaccharide conjugate that has inhibited the interaction between the heparin/heparan sulfate and the protein.

Different anionic oligosaccharide conjugates will interact with different ligands, or different ligands will interact with different anionic oligosaccharide conjugates or both. Accordingly, another assay involves the use of affinity columns carrying immobilized ligands. The anionic oligosaccharide conjugates are then passed through the column and the presence of retardation of the anionic oligosaccharide conjugates determined. A salt gradient is conveniently used to elute bound anionic oligosaccharide conjugates. Once a fraction that binds to a ligand on a column is identified, the fraction can be further analyzed to obtain an indication of the number of different structural entities therein. Such analysis may comprise, for example, anion exchange chromatography, mass spectrometry or electrophoresis.

Other examples of assays contemplated by the present invention include functional assays such as whole cell assays to assess cell proliferation (such as shown in Examples 11 to 13), enzyme inhibition assays (such as shown in Example 14), chemotaxis assays (such as shown in Example 15) and animal assays (such as shown in Examples 16 to 20). Such functional assays may provide more useful information on the effect of the tested anionic oligosaccharide conjugate(s) than pure binding assays.

Once anionic oligosaccharide conjugates that bind to a particular ligand have been identified, this fraction itself may be useful as a therapeutic to inhibit interaction between a protein (or other ligand) and a cell surface GAG (e.g. heparin or heparan sulfate). The protein (or other ligand) may be cell free or associated with a cell or virus such as a cell surface or viral surface. The said anionic oligosaccharide conjugate may also be useful as a therapeutic to modulate interaction between a secreted cellular product and extracellular matrix components or between a cell surface protein and extracellular matrix components, or between a protein and its ligand, both or either of which may be cell surface or cell associated. Alternatively, the anionic oligosaccharide conjugate may be used as a target to identify natural products or products from a chemical library that mimic the anionic oligosaccharide conjugate in terms of binding to a ligand or that inhibits or promotes the interaction between the GAG and the ligand. These molecules may be antagonists or agonist or chemical analogs of the GAG. Hence, an "analog" extends to and encompasses any structure which is functionally equivalent in that it binds and/or modulates a ligand in an analogous manner.

Reference herein to "modulate" or "modulation" extends to and encompasses inhibiting and/or promoting an interaction.

Accordingly, another aspect of the present invention is directed to a method for generating a medicament for treating a disease condition in a subject, said method comprising producing a range of anionic oligosaccharide conjugates according to the process of the invention, and screening each anionic oligosaccharide conjugate for an ability to interact with or modulate the ligand. The anionic oligosaccharide conjugate that interacts with or modulates the ligand is identified and using same or an analog, agonist or antagonist thereof in the manufacture of said medicament.

In one preferred embodiment, the modulation is an inhibition.

Types of ligands contemplated herein include those listed above such as PECAM-1, Cyclophilin A, gp120 and cytokines such as interleukin (IL)-1, 2, 3, 4, 5, 6, 7, 8, 10, 11, 12, 13, 14, 15 and 17 (including IL-25), G-CSF, GM-CSF, LIF, and M-CSF and chemokines such as eotaxin-1, eotaxin-2 and eotaxin-3 and enzymes such as elastase and other chemoattractants such as MCP-1 and MIP-1$\alpha$.

The subjects to be treated include humans, livestock animals (e.g. cattle, sheep, pigs, horses, donkeys), laboratory test animals (e.g. rabbits, guinea pigs, mice, rats) and companion animals (e.g. dogs, cats).

Yet another aspect of the present invention contemplates a method of prophylaxis and/or treatment of a disease condition in a subject, said disease condition resulting from interaction between a GAG on a surface of a cell in said host and a ligand, or a GAG in the extracellular matrix in said host and a ligand that may or may not be cell associated, or a protein-ligand interaction in said host that can be disrupted by a GAG where the protein may be cell associated and the ligand soluble or both protein and ligand may be cell associated, said method comprising administering to said subject a therapeutically effective amount of an anionic oligosaccharide conjugate, produced and identified according to the invention, that interacts with said ligand.

Another aspect of the present invention provides a pharmaceutical composition comprising an anionic oligosaccharide conjugate as defined herein and a pharmaceutically acceptable carrier and/or diluent.

The pharmaceutical forms suitable for injectable use include sterile aqueous solutions (where water soluble), sterile powders for the extemporaneous preparation of sterile injectable solutions and inhalable forms. Such forms are preferably stable under the conditions of manufacture and storage. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of surfactants. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the anionic oligosaccharide conjugate and carrier/diluent in the required amount in the appropriate solvent followed by sterilization or at least a process to reduce contaminating viruses, bacteria or other biological entities to acceptable levels for administration to a human or animal subject. In the case of sterile powders for the preparation of sterile injectable solutions, suitable methods of preparation include vacuum drying and the freeze-drying technique that yields a powder of active ingredient plus any additionally desired ingredient.

When the anionic oligosaccharide conjugate is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should preferably contain at least 1% by weight of active anionic oligosaccharide conjugate. The percentage of the compositions and preparations may, of course, be varied and may conveniently be between about 5 to about 80% of the weight of the unit. The amount of active anionic oligosaccharide conjugate in such therapeutically useful compositions is such that a suitable dosage will be obtained. Preferred compositions or preparations according to the present invention are prepared so that an oral dosage unit form contains between about 0.1 μg and 200 mg of active anionic oligosaccharide conjugate. Alternative dosage amounts include from about 1 μg to about 1000 mg and from about 10 μg to about 500 mg. These dosages may be per individual or per kg body weight. Administration may be per second, minute, hour, day, week, month or year.

The tablets, troches, pills and capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and anti-fungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

The composition may also be formulated for local or topical administration. Techniques formulation and administration may be found in "Remington's Pharmaceutical Sciences", Mack Publishing Co., Easton Pa., 16th edition, 1980, Ed. By Arthur Osol. Thus, for local or topical administration, the subject compositions may be formulated in any suitable manner, including, but not limited to, creams, gels, oils, ointments, solutions, suspensions, powders, mists or aerosols. For transmucosal administration, penetrants appropriate to the barrier to be permeated are used in the formulation. Such penetrants are generally known in the art and include, but are not restricted to, benzalkonium chloride, digitonin, dihydrocytochalasin B5 and capric acid.

The compositions of the subject invention in the form of lotions, creams or gels may contain acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, buffering agents, cellulose derivatives, emulsifying agents such as nonionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

In one particularly preferred embodiment, the present invention contemplates an inhalant pharmaceutical composition. The compositions comprising one or more anionic oligosaccharide conjugates of the present invention may be administered to the respiratory tract as a nasal or pulmonary inhalation aerosol or solution for a nebuliser, or as a microfine powder (preferably with particles of the order of 1 to 10 microns in size or less) for insufflation, alone or in combination with an inert carrier such as lactose, or with other pharmaceutically acceptable excipients.

Aerosol formulations include those in which the anionic oligosaccharide conjugate is provided in a pressurized pack with a suitable propellant such as a prerssurised metered dose inhaler (pMDI). Whilst the propellant may be a chlorofluorocarbon (CFC) such as dichlorodifluoromethane, trichlorofluoromethane, dichlorotetrafluoroethane, the propellant is more preferably a non-chlorofluorocarbon propellant such as carbon dioxide, hydrofluoroalkanes (such as HFA-134a) or another suitable gas. The aerosol may conveniently also contain a surfactant such as lecithin. The dose of the anionic oligosaccharide conjugate may be controlled by provision of a metered valve. It has been found that a particle size of approximately 2 to 3 μm is preferable for the treatment of asthma, as particles smaller than 1 μm are generally exhaled without delivery to the lung, and particles larger than 10 μm are mostly trapped by oropharyngeal deposition and do not reach the lung. Devices propelled by HFA-134a deliver smaller droplets which penetrate more readily into the bronchial airways. Preferably the delivery of approximately 40% of the inhaled droplets into the lung is desirable and achievable using an pMDI as outlined above. For the treatment of allergic rhinitis the preferred particle size for drug delivery via the nasal passage is 20-80 μm, as smaller particles (less than 10 μm) get carried into the tracheobrachial region, whilst bigger particles (greater than 100 μm) get rapidly cleared from the nasal passageway.

The anionic oligosaccharide conjugate may also be provided in a pharmaceutical formulation which forms a gel in the nasal cavity. The anionic oligosaccharide conjugate may also be formulated in a powder composition which may be presented in unit dose form for example in capsules or cartridges of eg gelatin, or blister packs from which the powder may be administered by means of an inhaler.

As used herein the expression "pharmaceutically acceptable salt" refers to the salt of a given compound, wherein the salt is suitable for administration as a pharmaceutical. For example, such salts may be formed by the reaction of an acid or a base with an amino or a carboxyl group respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "protecting group" refers to any group which when bound to one or more hydroxyl, thiol, amino or carboxyl groups of the compounds prevents reactions from occurring at these groups and which protecting group can be removed by conventional chemical or enzymatic steps to re-establish the hydroxyl, thio, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in T. W. Greene and P. G. M. Wuts, "Protective Groups in Organic Synthesis" 2.sup.nd Ed., 1991, John Wiley and Sons, N.Y.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

"Selectivity" or "specificity" in general is a measure of the binding preferences of a ligand for different receptors and/or a measure of the binding preferences of different ligands for a receptor. The selectivity of a ligand with respect to its target receptor relative to another receptor is given by the ratio of the respective values of $K_d$ (i.e., the dissociation constants for each ligand-receptor complex), or in cases where a biological effect is observed below the $K_d$, selectivity is given by the ratio of the respective $EC_{50}$ values (i.e. the concentrations that produce 50% of the maximum response for the ligand interacting with the two distinct receptors).

The term "therapeutically effective amount" refers to that amount which is sufficient to effect treatment, as defined above, when administered to an animal, preferably a mammal, more preferably a human in need of such treatment. The therapeutically effective amount will vary depending on the subject and disease state being treated, the severity of the affliction and the manner of administration, and may be determined routinely by one of ordinary skill in the art.

The term "treatment" as used herein covers any treatment of a condition or disease in an animal, preferably a mammal, more preferably a human, and includes: (i) preventing the disease or condition from occurring in a subject which may be predisposed to the disease but has not yet been diagnosed as having it; (ii) inhibiting the disease or condition, i.e. arresting its development; (iii) relieving the disease or condition, i.e. causing regression of the condition; or (iv) relieving the conditions caused by the disease, i.e. symptoms of the disease.

It is understood that the compounds of the present invention may exist in one or more stereoisomeric forms (eg enantiomers, diastereomers). The present invention includes within its scope all of these stereoisomeric forms either isolated (in for example enantiomeric isolation), or in combination (including racemic mixtures).

The invention will now be described with reference to the following non-limiting examples:

EXAMPLES

Example 1

Synthesis of N'-Fmoc-1-N-glycinamidomaltotrioside

Numerous examples exist in the prior art for the formation of glycosylamines, the methods of which are applicable to a diverse range of oligosaccharide conjugates.

Briefly, maltotriose (1 g, ~2 mmol) and $NH_4HCO_3$ (160 mg, 2 mmol) were dissolved in ammonia (10 mL). The solution was incubated for 32 hours at 40° C. before evaporation to dryness in a centrifugal evaporator. To remove residual ammonia, the residue was dissolved in the minimum of water and lyophilized. A portion of the residue (820 mg) was dissolved in a mixture of DMSO (10 mL), DMF (6 mL) and DIPEA (0.6 mL). Fmoc-glycine (1.2 g), HOBT (0.5 g) and HBTU (3 g) were added and the solution was incubated for at least 4 hrs before addition of an equal volume of water and acidified with acetic acid (0.6 mL) to quench the reaction. After cooling and filtering, the desired product can be purified by preparative RP-HPLC. For example, up to 2 mL was injected on a 250 mm×10 mm ID Exsil C18 column. The column was eluted with a binary gradient mixture of solvent A (0.1% TFA containing 15% acetonitrile) and solvent B (85% acetonitrile). The gradient comprised 10% B for 3 minutes, increased to 50% at 15 minutes (to elute the desired product), and then 90% at 16 minutes which was maintained for 5 minutes (to elute Fmoc-glycinamide and excess Fmoc-gly). The flow rate was 2.5 mL/min. The eluent was monitored at 290 nm and fractions collected by an autosampler. Fractions containing the desired product were pooled, concentrated in a centrifugal evaporator to remove most of the acetonitrile and then lyophilized to afford a fluffy, white powder (~0.6 g).

N'-Fmoc-1-N-glycinamido derivatives of other oligosaccharides were prepared in a similar manner.

Example 2

Synthesis of N'-Fmoc-1-N-glycinamidomaltotrioside polysulfate

N'-Fmoc-1-N-glycinamidomaltotrioside (0.5 g, 0.64 mmol) was dissolved in dry DMF (10 mL) and pyridine sulfur trioxide complex (3 g, 19 mmol) added. The solution was incubated at room temperature for 48 hrs and quenched by the addition of water. Analysis of the reaction mixture by RP-IP HPLC with dual UV and ELSD indicated a single broad peak, indicating that no deprotection occurred. The desired product can be purified by preparative RP-HPLC, RP-IP HPLC or AEX chromatography. For example, up to 2 mL was injected on a 250 mm×10 mm ID Exsil C18 column. The column was eluted with a binary gradient mixture of solvent A (0.1% TFA) and solvent B (50% acetonitrile). The gradient comprised 6% B for 3 minutes, increased to 50% at 15 minutes. The flow rate was 2.5 mL/min. The eluent was monitored at 290 nm and fractions collected by an autosampler. Fractions containing the desired product were pooled and concentrated to dryness in a centrifugal evaporator. The product was analysed by MALDI MS using the ion-pair crystallisation technique shown in FIG. 1. The spectrum clearly indicates that the product is persulfated.

Example 3

Synthesis of Chloroacetyl Building Block A (Scheme 1) for Maltotriose Series

Water and NaHCO$_3$ (0.2 g) were added to N'-Fmoc-1-N-glycinamidomaltotrioside polysulfate and adjusted to pH 12.5 by the addition of 10 M NaOH. The Fmoc protected product dissolved fully as the pH was increased, after which a precipitate formed. Analysis of the reaction mixture by RP-IP HPLC indicated complete deprotection within 20 minutes. The pH was adjusted to 8.5 by the addition of acetic acid and the aqueous solution extracted with CHCl$_3$ (3×10 mL) and hexane (1×10 mL). Chloroacetic anhydride (0.5 g) and NaHCO$_3$ (1 g) were added to the aqueous solution and, periodically, the pH was adjusted to 8.25 by the addition of NaHCO$_3$. After 1 hr, analysis of the reaction mixture by RP-IP HPLC indicated complete reaction. The product was purified by AEX after first acidifying the reaction to pH 6 by the addition of 2 M HCl and 5 M NaCl added to render a final concentration of approximately 0.3 M NaCl. The solution was applied to a 5 mL Econo-Q cartridge (Biorad, Sydney, Australia) and washed with 10 mM NaH$_2$PO$_4$/0.6 M NaCl pH 7 and the product eluted with 10 mM NaH$_2$PO4/3M NaCl pH 7 and stored at 4° C. until further use. The product concentration was assayed by RP-IP HPLC using sucrose octasulfate as a quantitative standard.

Example 4

Synthesis of Building Block C (Scheme 1) for Maltotriose Series

Aliquots of the chloroacetyl Building Block A were adjusted to pH 8.25 by the addition of NaHCO$_3$, isopropanol added to generate a 30% solution and a 10-fold molar excess of a dithiol chosen from Dithiols 1 to 5 shown above. The solution was stirred at room temperature overnight. The excess dithiol was extracted with CHCl$_3$ (3×10 mL) and hexane (1×10 mL). In instances where analysis indicated formation of disulfides these were reduced by addition of TCEP (solid) 1 hr prior to purification by AEX as described above. The purified products were assayed by RP-IP HPLC using sucrose octasulfate as a quantitative standard and stored at 4° C. until further use. In this manner, each of the 5 dithiol building blocks, corresponding to coupling of maltriose Building Block A with each of the linkers, were synthesised in parallel.

Example 5

Synthesis of Bisinaltotriosyl Polysulfate Final Products

A 1.5 molar excess of the maltotriose Building Block A was mixed with each of the maltotriose Building Blocks C and the pH adjusted to 9. The solutions were incubated at room temperature for 2 days. At this point neither residual maltotriose Building Block C or disulfide products were detected using analysis by RP-IP with ELSD. When disulfide products were detected after a few hours, these could be reduced by the addition of TCEP. If desired, the TCEP can be removed by AEX as described above. In which case, the collected fractions are adjusted to pH 9 and the reaction allowed to proceed further, if necessary with further addition of Building Block A.

At the desired end point, the reactions were diluted with an equal volume of 15 mM tributylammonium acetate pH 6 containing 15% acetonitrile and the products purified by RP-IP HPLC using a 250 mm×10 mm ID Exsil C18 column. The column was eluted with a binary gradient mixture of solvent A (15 mM tributylammonium acetate pH 6 containing 15% acetonitrile) and solvent B (85% acetonitrile). The gradient comprised 10% B for 3 minutes, increased to 50% at 20 minutes, and then 90% at 22 minutes which was maintained for 5 minutes. The flow rate was 2.5 mL/min. The eluent was monitored at 254 nm and fractions collected by an autosampler. Fractions containing the desired product were pooled, concentrated in a centrifugal evaporator to remove most of the acetonitrile and then lyophilized to afford a fluffy, white powder.

Example 6

A mixture of oligosaccharides of varying D.P. can be used as a feedstock. Fractionation of this mixture on the basis of size is achieved by preparative RP HPLC after attaching a hydrophobic Fmoc protecting group. With this mode, retention decreases as the oligosaccharide size increases. The Fmoc group is attached via a glycosylamine intermediate. Sulfation of the oligosaccharide-Fmoc conjugate is achieved with Py.SO₃ complex and the product extracted from the reaction mixture using preparative RP-IP HPLC. Subsequent deprotection and bromoacetylation of the amine is done in one-pot and yields a bromoacetyl derivative. This is reacted (in excess) with Dithiol 2 to generate the final product (X=H or SO₃Na):

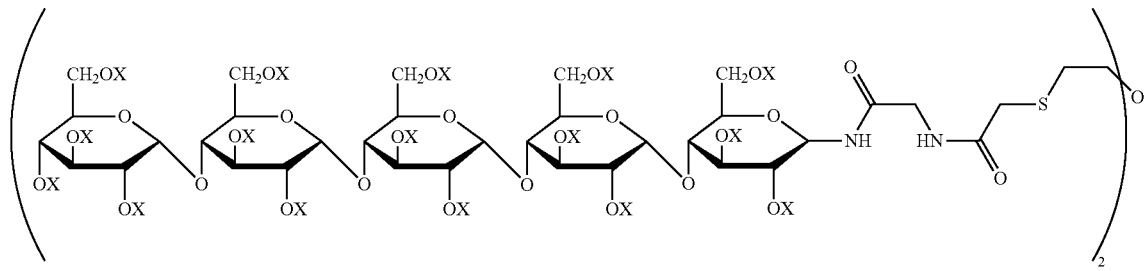

The ion-paring agent used during the HPLC steps, tributylamine, is inert during these manipulations. The desired product is purified by preparative RP-IP HPLC.

An outline of the synthetic route to the preparation of sulfomaltopentaose-tetraethylenglycol-sulfomaltopentaose is shown in Scheme 2 and described below. For clarity, only a portion of each of the maltopentaose chains are depicted in the scheme.

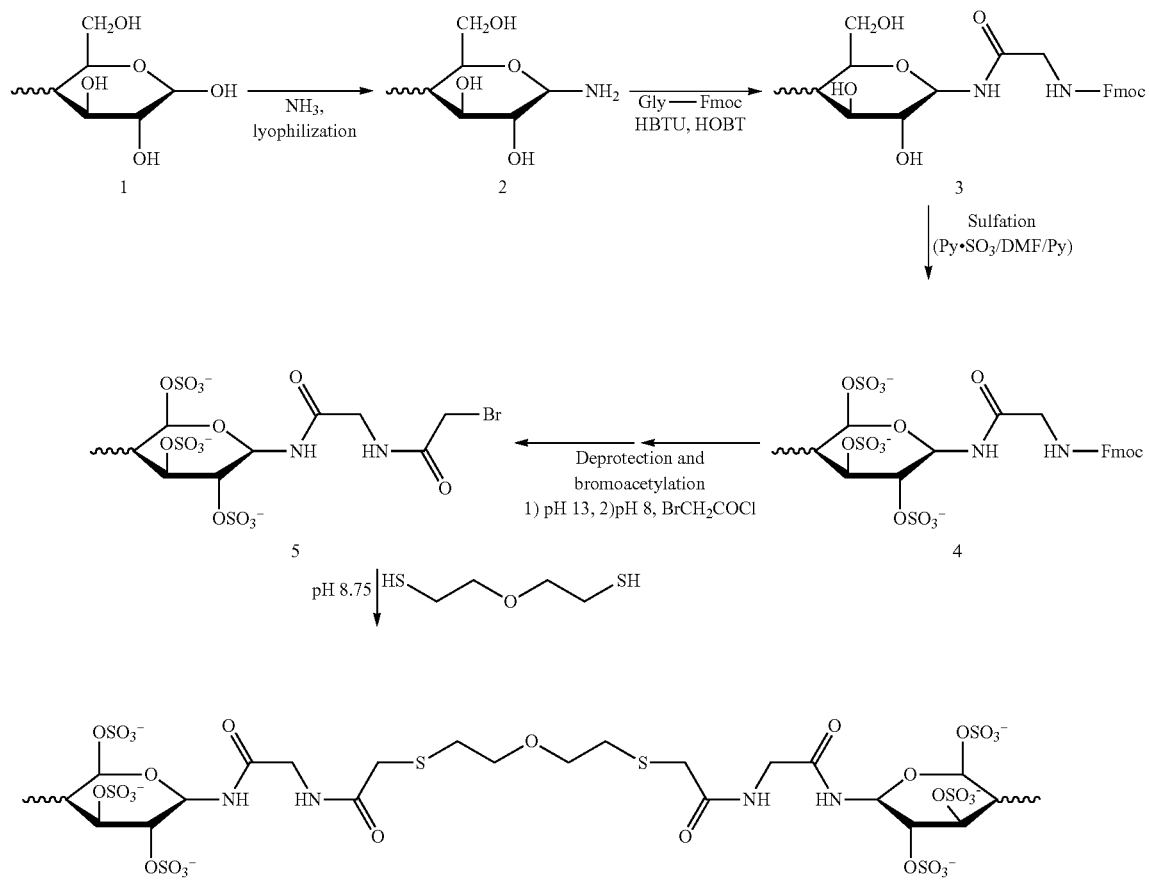

Figure 2:
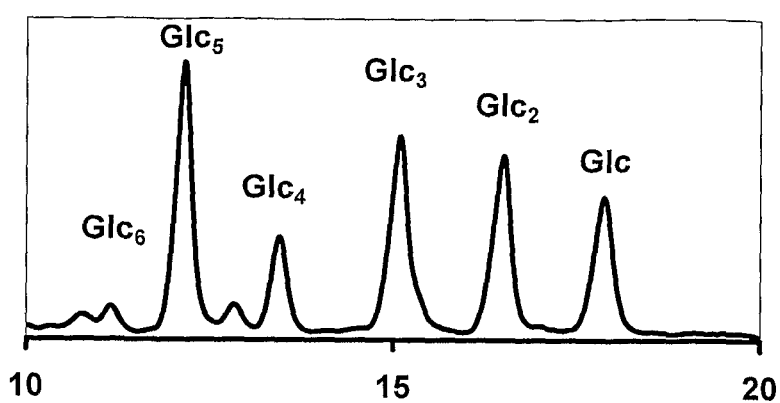
FIG. 2 shows the elution profile for preparative HPLC purification of Fmoc derivatives of malto-oligosaccharides (prepared from "Pentrup syrup").

Procedure:
1. Malto-oligosaccharide syrup (e.g. Hayashibara pentrup syrup or corn syrup, 50 g) and $NH_4HCO_3$ (6 g) were dissolved in 25% ammonia (375 mL) and incubated at 40° C. for 40 hrs. The mixture was rotary evaporated to dryness, dissolved in the minimum of water and evaporated to dryness again. The residue was dissolved in the minimum of water and 3 volumes of ethanol added with mixing. The mixture was allowed to settle overnight and the supernatant decanted. The residue was dissolved in a minimum of water and evaporated to dryness again to yield compound 2 of Scheme 2 as a gum.
2. Fmoc-gly-OH (11 g), hydroxybenzotriazole (HOBT, 27.5 g), O-benzotriazole-N,N,N',N'-tetramethyl-uronium-hexafluoro-phosphate (HBTU, 4.9 g) and TEA (4.9 mL) were dissolved in a mixture of 120 mL DMSO and 30 mL DMF. The resulting solution was added to the oligosaccharide residue and the mixture stirred overnight. The reaction was quenched by addition of water (500 mL) and glacial acetic acid (5 mL) and allowed to cool to room temperature. The precipitate formed was removed and discarded. The liquor was washed with ethyl acetate (3×100 mL) and hexane (1×100 mL). Residual ethyl acetate and hexane in the aqueous layer were removed by concentrating in a rotary evaporator and the solution diluted to 600 mL by the addition of water.
3. The mixture was fractionated by preparative reversed-phase HPLC by repeated injection.
    Example Conditions—
    Column: Phenomenex Axia 100×21.2 mm Luna C18 (2) fitted with a security guard cartridge (or suitable substitute).
    Eluent A: 0.1% formic acid.
    Eluent B: 80% acetonitrile.
    Flow: 20 mL/min.
    Detector: UV at 270 nm.
    The desired fraction was collected and concentrated in a rotary evaporator and the resulting solution lyophilised to yield approximately 6 g of white powder of the Fmoc derivative of maltopentaose ($M_5$gly-Fmoc) derived from pentrup syrup. The HPLC elution profile is shown in FIG. 2.
4. $M_5$gly-Fmoc (6 g) was dissolved in DMF (100 mL), $Py.SO_3$ complex (42 g) added and the solution stirred at room temperature overnight. The reaction was quenched by addition of water (500 mL) and adjusted to pH 6 by addition of tributylamine. The sulfated $M_5$gly-Fmoc was extracted using preparative reversed-phase ion-pairing HPLC by repeated injection.
    Example Conditions—
    Column: Phenomenex Axia 100×21.2 mm Luna C18 (2) fitted with a security guard cartridge (or suitable substitute).
    Eluent A: 8 mM tributylamine in 20% acetonitrile adjusted to pH 5.8 with acetic acid.
    Eluent B: 80% acetonitrile.
    Flow: 20 mL/min.
    Detector: UV at 270 nM.
    The desired fraction(s) are concentrated in a rotary evaporator to yield a solution of the sulfated compound 4 from Scheme 2 ($SM_5$gly-Fmoc).
5. $SM_5$gly-Fmoc was deprotected by adjusting to >pH 13 with NaOH and incubated at room temperature for 15 minutes. The ppt/oil was extracted with 2×50 mL hexane and discarded. The resulting amine was bromoacetylated in the same pot after adjusting to pH 8.25. 3×1.2 g aliquots of bromoacetyl chloride were added at 15 minute intervals to the solution with constant pH monitoring and addition of $Na_2CO_3$ to maintain pH 8-8.25. The progress of this reaction was monitored by analytical RP-IP HPLC
    Example Conditions—
    Column: Phenomenex Luna 30×4.6 mm C18 (2) fitted with a security guard cartridge.
    Eluent A: 8 mM tributylamine in 20% acetonitrile adjusted to pH 5.8 with acetic acid.
    Eluent B: 80% acetonitrile.
    Flow: 1 mL/min.
    Detector: UV @ 270 nM and ELSD.
    The desired bromoacetylated derivative was precipitated by addition of 3 volumes of ethanol and the mixture cooled to 4° C. The precipitate was separated and redissolved in 0.4 M AcONa pH 7 and re-precipitated by addition of 3 volumes of ethanol and the mixture cooled to 4° C. The solid, corresponding to compound 5 of Scheme 2, was dissolved in the minimum of water and assayed by SEC as described above using β-cyclodextrin sulfate as a standard.
    To a solution containing approximately 450 mg of compound 5 from Scheme 2 was added 0.2M EDTA (200 μL), 1M $NaHCO_3$ (2 mL) and adjusted to pH 8.75. Isopropanol (3 mL) and 2,2'-oxydiethanethiol (17 μL) were added and the mixture stirred at room temperature. After 30 minutes, a further 17 μL 2,2'-oxydiethanethiol is added and the solution stirred overnight. The reaction was monitored by RP-IP HPLC as described above. The reaction was monitored by analytical RP-IP HPLC as described above. The transient intermediate resulting from the condensation of one bromoacetyl conjugate with a single thiol of the tetraethyleneglycol is also observed by this technique.
6. Compound 7 from Scheme 2 was purified by preparative RP-IP HPLC as described above. The appropriate fraction is concentrated by rotary evaporation and lyophilised to remove excess tributylamine acetate.
7. The residue was dissolved in water and the resulting solution adjusted to pH 5.5 with acetic acid. This solution is applied to a 4×2 cm column of Dowex 50WX8 ($Na^+$ form) 2×4 cm and washed with 3 column volumes of water. The flow through and washings are collected and pooled.
8. The pooled washings were adjusted to pH 7 and dialysed by repeated ultrafiltration with a 1 kDa MWCO membrane.
9. The concentrated solution was lyophilised to yield a white powder.

Example 7

Conjugates of maltooligosaccharides of different D.P. are prepared in a similar manner by selecting the appropriate fraction at step 3 in example 6 above.

Example 8

Conjugates of other oligosaccharides are prepared in a similar manner by selecting the appropriate pure oligosaccharide fraction of oligosaccharide mixture at step 1 in example 6 and subsequently selecting the appropriate fraction at step 3.

Example 9

Conjugates of oligosaccharides with a different linker are prepared by substituting a different dithiol compound at step 5 in example 6.

In a similar manner, the dithiol compound can be varied in the procedures of examples 7 and 8.

Example 10

BIAcore Screening Assay

The optical phenomenon of surface plasmon resonance is used to monitor physical interactions between molecules. Passing a solution of a potential protein ligand (e.g. IL-4, IL-5, eotaxin-1, eotaxin-2, IL-8 or MCP-1) over a sensor surface to which a target (e.g. heparin) is coupled monitors the real-time binding of protein ligands to the immobilized target. Detection is achieved by measuring refractive index changes very close to the sensor surface. When the refractive index is altered, the angle at which plasmon resonance occurs changes and this change directly correlates with the amount of protein interacting with the surface. A BIAcore 2000 is conveniently used. It is very sensitive and its microfluidics ensures that only small amounts of material are required.

Biotinylated heparin is immobilized on the biosensor chip. Biotinylation occurs via amino groups, or reducing termini modified with ammonia by reductive amination, using sulfo-NHS-biotin. Solutions containing potential protein ligands of interest are injected over the sensor chip surface, and the binding is measured in real time (Fernig, In: Proteoglycan protocols, Ed. R. V. Iozzo, Humana Press, Totowa, N.J., USA, 2001). Baculovirus expressed recombinant human IL-4 (rhIL-4) and baculovirus expressed recombinant human IL-5 (rhIL-5) readily bind to heparin immobilized by this method (see PCT/AU2005/000551). Binding is specific, as there is little interaction of either IL-4 or IL-5 with sensor chips that lack heparin. Similarly, recombinant human eotaxin-1 (CCL11) expressed in *E. coli* binds readily to immobilized heparin and binding is specific as there is little eotaxin binding to sensor chips lacking heparin (see 30544601 PCT glycan151). Similarly recombinant human IL-8 (CXCL8), MCP-1 (CCL2) and eotaxin-2 (CCL24) expressed in *E. coli* binds readily to immobilized heparin and binding is specific as there is little binding to sensor chips lacking heparin.

Preparations of the various anionic oligosaccharide conjugates of sulfated oligosaccharides inhibit the binding of IL-4, IL-5, eotaxin-1, eotaxin-2, IL-8 and MCP-1 to heparin immobilized on the BIAcore chip (Table 1 and Table 2).

Within each of the anionic oligosaccharide conjugates shown in the Tables that follow, the two oligosaccharides are the same. Such compounds are by no means meant to limit the anionic oligosaccharide conjugates of the present invention to those conjugates bearing identical oligosaccharide components $S^1$ and $S^2$. In some embodiments $S^1$ and $S^2$ are different oligosaccharides. Likewise, the fact that the oligosaccharides shown in the tables that follow are persulfated by no means limits the anionic oligosaccharide conjugates of the present invention to containing those oligosaccharides that are persulfated. In some embodiments the oligosaccharides are partially sulfated, and/or contain phosphate functionality, etc.

In the Tables that follow the linkers denoted by Et1, Et2, Et3, Et4 and Et5 are as depicted below:

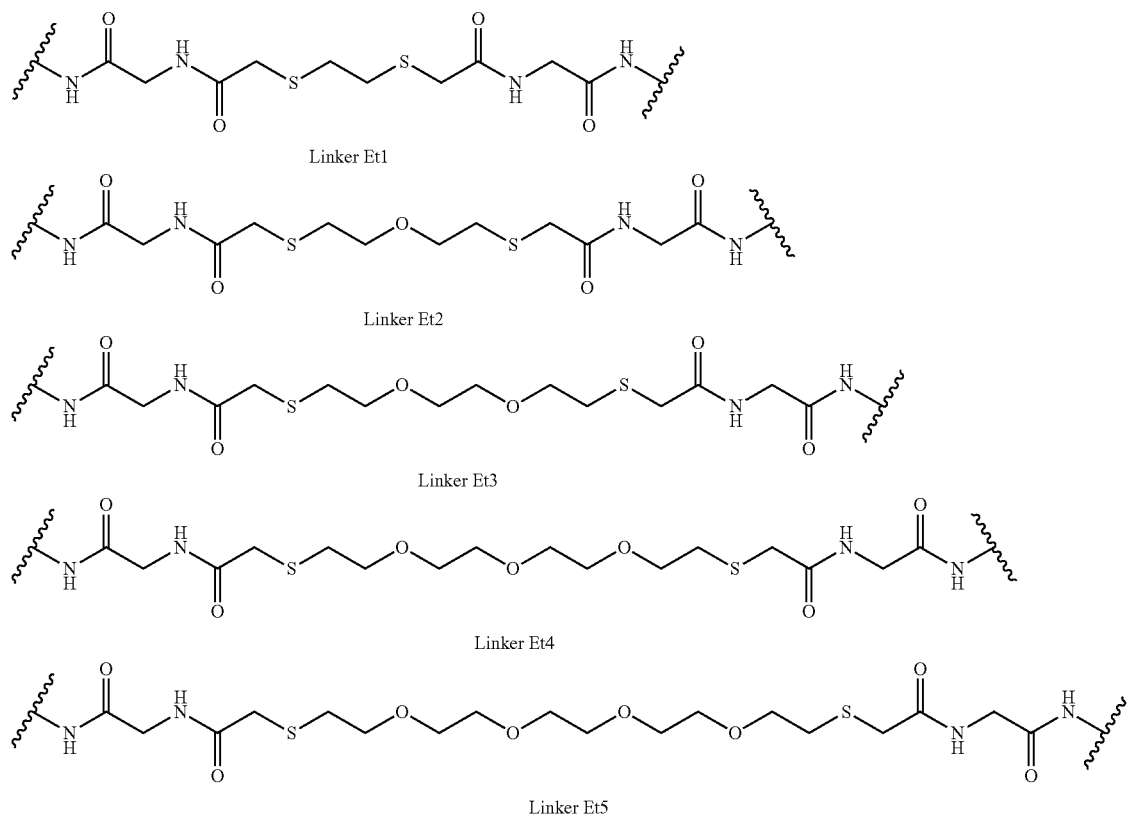

Linker Et1

Linker Et2

Linker Et3

Linker Et4

Linker Et5

It will be appreciated that linker Et1 may be formed using Dithiol 1, Et2 may be formed using Dithiol 2, Et3 may be formed using Dithiol 3, Et4 may be formed using Dithiol 4 and Et5 may be formed using Dithiol 5.

Some anionic oligosaccharide conjugates have far more activity than others. From these data the anionic oligosaccharide conjugates with the greatest activity are those of the linked sulfated-maltose series and in particular the linked sulfated maltopentaose conjugates. Although depending on the protein tested binding activity is also seen with linked sulfated maltotetraoses, this binding activity is not as great as that of the sulfated maltopentaose anionic oligosaccharide conjugate series. Anionic oligosaccharide conjugates comprising the sulfated maltopentaose structures bind far better to IL-8 and thereby inhibit IL-8 binding to heparin better than anionic oligosaccharide conjugates comprising the sulfated tetraose structures. The structural requirements for binding to MCP-1 are less stringent as both maltopentaose and maltotetraose containing anionic oligosaccharide conjugates bound approximately the same. MCP-1 can also bind conjugates based on a different saccharide backbone, but less well than the maltopentaose series. MCP-1 binds the linked sulfated xylans slightly better than it binds heparin and it appears that within this series sulfated xylopentaose anionic oligosaccharide conjugates linked by the smaller linkers, e.g. Et1 or Et3 are preferred.

The differences in the ability of Eotaxin-1 and Eotaxin-2 to bind the various anionic oligosaccharide conjugates are marked. Eotaxin-1 only binds the sulfated maltopentaose series, binding to about the same extent as heparin for anionic oligosaccharide conjugates with the Et2 and the Et5 linker, but binding is better than heparin when the anionic oligosaccharide conjugate contains the Et4 linker (Compound ID 9). In contrast Eotaxin-2 binds the sulfated maltopentaose series significantly better than heparin with the Et5 linker being slightly preferred. Eotaxin-2 also binds the sulfated maltotetraose series better than heparin, but within this series binding was better to an anionic oligosaccharide conjugate with a short linker (Et2 linker, Compound ID 12) rather than the long linker (Et5 linker, Compound ID 15). Eotaxin-2 did show some binding activity with the sulfated linked xylan series but this was weaker than the extent to which Eotaxin-2 bound to heparin.

The importance of linker length for binding varies from protein to protein. For Eotaxin-2, MCP-1 and IL-8 a sulfated maltopentaose with a Et5 linker (Compound ID 10) is preferred for greatest binding, whereas for Eotaxin-1 a sulfated maltopentaose with a Et4 linker (Compound ID 9) is preferred. The IL-4 binding data suggest that the length of the linker is of less importance so long as the linker does not become too long, as there was little difference between the sulfated maltopentaose with a Et2 linker (Compound ID 7) and a sulfated maltopentaose with a Et4 linker (Compound ID 9), but a sulfated maltopentaose with a Et5 linker had reduced binding capability. In contrast, IL-5 seems to require a sulfated maltopentaose with a Et4 linker (Compound ID 9) for best binding. Thus, the efficacy of the compounds varies according to their underlying structure and according to the protein involved in heparin binding and it is not obvious prior to screening which of the anionic oligosaccharide conjugates will be most effective.

These data also indicate that the anionic oligosaccharide conjugates bind to IL-4 at the site where heparin binds and that the binding of the anionic oligosaccharide conjugates to this region is more stable than that of heparin binding. These data similarly indicate that the anionic oligosaccharide conjugates bind to IL-5 at the site where heparin binds and that it's binding to this region is more stable than that of heparin binding.

TABLE 1

Ability of various anionic oligosaccharide conjugates to inhibit the binding of chemokines to heparin immobilized on a BIAcore biosensor surface

| | Persulfated | | % Inhibition of chemokine binding to heparin chip | | | |
|---|---|---|---|---|---|---|
| ID | oligosaccharide | Linker | Eotaxin-1 | Eotaxin-2 | IL-8 | MCP-1 |
| 1 | Maltotriose | Et1 | | | | |
| 2 | Maltotriose | Et2 | | | | |
| 3 | Maltotriose | Et3 | | | | |
| 4 | Maltotriose | Et4 | | | | |
| 5 | Maltotriose | Et5 | | 166.7 | | 30.0 |
| 6 | Maltopentaose | Et1 | | | | |
| 7 | Maltopentaose | Et2 | 108 | 16.7 | 19 | 5.6 |
| 8 | Maltopentaose | Et3 | | | | |
| 9 | Maltopentaose | Et4 | 71.4 | 15 | 14.6 | 6.4 |
| 10 | Maltopentaose | Et5 | 107.1 | 9.2 | 7.3 | 2.4 |
| 11 | Maltotetraose | Et1 | | | | |
| 12 | Maltotetraose | Et2 | >200 | 33.3 | 116.7 | 7.5 |
| 13 | Maltotetraose | Et3 | | | 187.5 | |
| 14 | Maltotetraose | Et4 | | | 125.0 | |
| 15 | Maltotetraose | Et5 | | 66.7 | >200 | 15 |
| 66 | Chitotetraose | Et1 | | | | |
| 67 | Chitotetraose | Et2 | >200 | >200 | >200 | >200 |
| 68 | Chitotetraose | Et3 | | | | |
| 69 | Chitotetraose | Et5 | | | | |
| 70 | Chitopentaose | Et1 | | >200 | | |
| 71 | Chitopentaose | Et2 | | | | |
| 72 | Chitopentaose | Et3 | | | | |
| 73 | Chitopentaose | Et4 | | | | |
| 74 | Chitopentaose | Et5 | | | | |
| 75 | Xylotetraose | Et1 | >200 | 83.3 | | 82.5 |
| 76 | Xylotetraose | Et2 | | | | |
| 77 | Xylotetraose | Et3 | | 166.7 | | |
| 78 | Xylotetraose | Et4 | | | | |
| 79 | Xylotetraose | Et5 | | 166.7 | | |
| 80 | Xylopentaose | Et1 | >200 | 125 | >200 | 61.9 |
| 81 | Xylopentaose | Et2 | | | | |
| 82 | Xylopentaose | Et3 | >200 | | >200 | 75 |
| 83 | Xylopentaose | Et4 | | | | |
| 84 | Xylopentaose | Et5 | | 125 | >200 | 84.4 |
| | Heparin | | 100 | 100 | 100 | 100 |

Anionic oligosaccharide conjugate data are expressed as a % relative to heparin concentration required to inhibit chemokine binding by 50%. The percentage is set at 100% for heparin. Values below 100% indicate that the anionic oligosaccharide conjugates are better than heparin at binding to the chemokine and blocking its binding to heparin on the chip. Conversely, values above 100% indicate that the inhibitors are worse than heparin at blocking the chemokines from binding to heparin on the chip.

TABLE 2

Ability of various anionic oligosaccharide conjugates to inhibit the binding of IL-4 and IL-5 to heparin immobilized on a BIAcore biosensor surface

| ID | Persulfated oligosaccharide | Linker | % IL-4 binding* End point heparin | % IL-4 binding* Biotin-heparin | IC$_{50}$, nM End point heparin | % IL-5 binding* End point heparin | % IL-5 binding* Biotin-heparin | IC$_{50}$, nM Biotin-heparin |
|---|---|---|---|---|---|---|---|---|
| 1 | Maltotriose | Et1 | | 31% | | | | |
| 2 | Maltotriose | Et2 | | 33% | 12000 | | | >20000 |
| 3 | Maltotriose | Et3 | | 39% | | | | |
| 4 | Maltotriose | Et4 | | 38% | | | | |
| 5 | Maltotriose | Et5 | | 37% | | | | |
| 6 | Maltopentaose | Et1 | | 0% | | | | |
| 7 | Maltopentaose | Et2 | | 0% | 33 | | | 350 |
| 8 | Maltopentaose | Et3 | | 0% | | | | 200 |
| 9 | Maltopentaose | Et4 | | | 25 | | | 50 |
| 10 | Maltopentaose | Et5 | | 0% | 120 | | | |
| 11 | Maltotetraose | Et1 | | 0% | | | | |
| 12 | Maltotetraose | Et2 | | 0% | | | | 800 |
| 13 | Maltotetraose | Et3 | | 5% | | | | |
| 14 | Maltotetraose | Et4 | | 23% | | | | |
| 15 | Maltotetraose | Et5 | | 0% | | | | |
| 66 | Chitotetraose | Et1 | 62% | 30% | | 95% | 89% | |
| 67 | Chitotetraose | Et2 | 13% | 4% | 1250 | 4% | 3% | 950 |
| 68 | Chitotetraose | Et3 | 99% | 68% | | 99% | 98% | |
| 69 | Chitotetraose | Et5 | 83% | 54% | | 92% | 89% | |
| 70 | Chitopentaose | Et1 | 100% | 60% | | 97% | 95% | |
| 71 | Chitopentaose | Et2 | 88% | 48% | | 95% | 90% | |
| 72 | Chitopentaose | Et3 | 100% | 69% | | 100% | 98% | |
| 73 | Chitopentaose | Et4 | 100% | 72% | | 100% | 99% | |
| 74 | Chitopentaose | Et5 | 83% | 46% | | 93% | 89% | |
| 75 | Xylotetraose | Et1 | 30% | 11% | 2500 | 73% | 60% | |
| 76 | Xylotetraose | Et2 | 54% | 27% | | 95% | 90% | |
| 77 | Xylotetraose | Et3 | 50% | 23% | | 94% | 87% | |
| 78 | Xylotetraose | Et4 | 57% | 30% | | 92% | 87% | |
| 79 | Xylotetraose | Et5 | 56% | 30% | | 94% | 90% | |
| 80 | Xylopentaose | Et1 | 25% | 8% | 1450 | 67% | 52% | 1000 |
| 81 | Xylopentaose | Et2 | 33% | 13% | | 77% | 65% | |
| 82 | Xylopentaose | Et3 | 31% | 12% | 2000 | 79% | 67% | |
| 83 | Xylopentaose | Et4 | 32% | 13% | | 83% | 72% | |
| 84 | Xylopentaose | Et5 | 26% | 10% | 2500 | 70% | 58% | |
| | Heparin | | | | 3300 | | | 37 |

Data are shown for two methods of immobilization of heparin:
Biotin-heparin = biotin labeling of amino groups;
End point heparin = biotinylation of reducing termini.
*The % of cytokine binding in the presence of the various anionic oligosaccharide conjugates relative to the level of binding obtained in the absence of anionic oligosaccharide conjugate was calculated with an anionic oligosaccharide conjugate concentration of 5 μM for ID 1-15; 8 μM for ID 66-74 and 10 μM for ID 75-84.

Example 11

Functional Analyses of Anionic Oligosaccharide Conjugates on the Asthma and Allergic Rhinitis Protein Target, IL-5

The various anionic oligosaccharide conjugates inhibited the proliferation of an IL-5 responsive cell line to differing degrees. This occurs at very low doses and is not due to a toxic effect of the anionic oligosaccharide conjugate as other similarly sulfated polysaccharides have no effect in this assay. These experiments are performed with the IL-5 responsive cells, Ba/F-IL-5. The Ba/F-IL-5 cells were derived from the Ba/F3 cell line.

The Ba/F3 cell line was transformed to be both IL-5 dependent and to express luciferase by co-transfection of the cells with pGL3 control vector (Promega, USA) and pEE6hcmv-IL-5Rα. The control vector, pGL3 expresses a modified luciferase under the direct control of the SV40 promoter and enhancer, but contains no selectable marker. To prepare pEE6hcmv-hIL-5Rα a full length human IL-5 receptor α chain (hIL-5R-α) was cloned by RT PCR from HL60 cells. The preparation of the Ba/F-IL-5 cells has been described by Coombe et al, *Journal of Immunological Methods* 215: 145-150, 1998. The Ba/F-IL-5 cells may be further modified by co-transfection with pPGK-puromycin-luciferase, a vector containing luciferase under the control of the SV40 promotor with the selectable marker puromycin.

After transfection, positive transfectants are selected in 3 μg/mL puromycin. The positive transfectants are then cloned to produce a line with detectable luciferase expression. The proliferation assays are carried out in 96-well microplates suitable for such assays (Falcon). The wells are flat bottomed, with white sides and a clear bottom. Cells are washed to remove any cytokine in the growth medium and then resuspended in RPMI/5% w/v FCS. The cells are counted with a Coulter Z2 Particle Counter and Size Analyzer (Coulter Electronics, England) and routinely $1.6 \times 10^4$ cells are added to microplate wells that contain either no IL-5 (negative control) or various dilutions of IL-5. When the effect of anionic oligosaccharide conjugates, or other sulfated polysaccharides is to be measured, the wells also contain various concentrations of these molecules.

The cells proliferate for 24 hours at 37° C. in a humidified atmosphere, after which the luciferase activity is measured by the addition of 50 µl of luciferase substrate buffer (50 mM Tris-HCl, pH 7.8, 15 mM $MgSO_4$, 33.3 mM DTT, 0.1 mM EDTA, 0.5 mM Na-luciferin, 0.5 mM ATP, 0.25 mM lithium Co A and 0.5% v/v Triton X-100). Immediately after the addition of the luciferase buffer the plate is assayed for luciferase activity. Light emissions are detected on a Victor 1420 Multi-label counter (Wallac, Turku, Finland). Using this assay it has been demonstrated that some of the anionic oligosaccharide conjugates are very effective inhibitors of IL-5 dependent Ba/F-IL-5 cell proliferation whereas others are less effective (Table 3).

The saccharide component of the anionic oligosaccharide conjugate seems to be important for activity. Both the size of the oligosaccharide and the underlying composition seems to be important. The linked pentasaccharides are more effective inhibitors than linked tetrasaccharides and of the linked pentasaccharides the linked sulfated maltose series was the most effective but the linked sulfated xylan pentasaccharides also displayed considerable activity, particularly at 10 µg/mL. The length of the linker does not appear to be that important in this assay although possibly the linkers Et4 and Et5 are preferred. Thus, the best of the linked sulfated maltopentaose series were IDs 7-10 and the best of the linked sulfated xylopentaose series were ID 83 and 84, with the linked sulfated chitosan series having little activity.

TABLE 3

The ability of the anionic oligosaccharide conjugates to inhibit IL-5 dependent cell proliferation

| | | | % Inhibition of Ba/F-IL-5 cell proliferation stimulated by IL-5 | |
|---|---|---|---|---|
| ID | Persulfated oligosaccharide | Linker | Anionic oligosaccharide conjugate (1 µg/mL) | Anionic oligosaccharide conjugate (10 µg/mL) |
| 1 | Maltotriose | Et1 | 0 | 39.6 ± 7.6 |
| 2 | Maltotriose | Et2 | 0 | 45.2 ± 7.6 |
| 3 | Maltotriose | Et3 | 1 ± 0.2 | 31.1 ± 4.9 |
| 4 | Maltotriose | Et4 | 1.1 ± 0.2 | 30.7 ± 4.5 |
| 5 | Maltotriose | Et5 | 7.1 ± 1.3 | 26.4 ± 3.3 |
| 6 | Maltopentaose | Et1 | 52.3 ± 6.8 | 63.5 ± 7.1 |
| 7 | Maltopentaose | Et2 | 41.5 ± 3.7 | 59.5 ± 7.4 |
| 8 | Maltopentaose | Et3 | 49.9 ± 5 | 62.3 ± 9.5 |
| 9 | Maltopentaose | Et4 | 45.3 ± 6.5 | 62.7 ± 8.8 |
| 10 | Maltopentaose | Et5 | 51.2 ± 5.2 | 59.7 ± 4.4 |
| 11 | Maltotetraose | Et1 | 15.1 ± 1.8 | 53.8 ± 6.3 |
| 12 | Maltotetraose | Et2 | 8.4 ± 1.1 | 46.1 ± 4.4 |
| 13 | Maltotetraose | Et3 | 4.7 ± 0.4 | 40 ± 5.1 |
| 14 | Maltotetraose | Et4 | 9.0 ± 1 | 39.8 ± 2.9 |
| 15 | Maltotetraose | Et5 | 6.2 ± 1.1 | 46.3 ± 7.5 |
| 66 | Chitotetraose | Et1 | 8.6 ± 1 | 16.1 ± 2.1 |
| 67 | Chitotetraose | Et2 | 8.2 ± 1.1 | 28.8 ± 4.8 |
| 68 | Chitotetraose | Et3 | 0 | 23.7 ± 4.5 |
| 69 | Chitotetraose | Et5 | 15.9 ± 2.4 | 33.8 ± 5.0 |
| 70 | Chitopentaose | Et1 | 12.6 ± 1.4 | 31.5 ± 3.2 |
| 71 | Chitopentaose | Et2 | 13.4± 1.4 | 29.8 ± 4.9 |
| 72 | Chitopentaose | Et3 | 7.8 ± 0.9 | 22.0 ± 3.3 |
| 73 | Chitopentaose | Et4 | 17.3 ± 1.9 | 34.4 ± 5.3 |
| 74 | Chitopentaose | Et5 | 22.4 ± 4.4 | 34 ± 3.4 |
| 75 | Xylotetraose | Et1 | 0 | 27.9 ± 3.5 |
| 76 | Xylotetraose | Et2 | 5.2 ± 0.5 | 33.1 ± 3.4 |
| 77 | Xylotetraose | Et3 | 2.7 ± 0.2 | 37.2 ± 2.4 |
| 78 | Xylotetraose | Et4 | 6.4 ± 0.6 | 35.3 ± 2.0 |
| 79 | Xylotetraose | Et5 | 8.8 ± 0.8 | 30.3 ± 1.6 |
| 80 | Xylopentaose | Et1 | 16.9 ± 1.3 | 54.7 ± 4.7 |
| 81 | Xylopentaose | Et2 | 14.7 ± 1.2 | 57.1 ± 8.4 |
| 82 | Xylopentaose | Et3 | 14.4 ± 1.8 | 53.5 ± 5.9 |
| 83 | Xylopentaose | Et4 | 20.6 ± 1.9 | 57.1 ± 6.7 |
| 84 | Xylopentaose | Et5 | 21.1 ± 2 | 57.7 ± 6.2 |

Example 12

Functional Analyses of Anionic Oligosaccharide Conjugates on the Asthma Target Protein, IL-4

The various anionic oligosaccharide conjugates inhibited the proliferation of an IL-4 responsive cell line to differing degrees. This occurs at very low doses and is not due to a toxic effect of the anionic oligosaccharide conjugate because other, similarly sulfated polysaccharides, at the same concentrations of IL-4 and polysaccharide have no effect. These experiments utilize the TF-1.8 cells. TF-1.8 cells are a subclone of the TF-1 cells that have been selected for growth in IL-4 or IL-5. TF-1 cells were originally established from a bone marrow sample from a male with severe pancytopenia. These cells are dependent on IL-3 or GM-CSF for long term growth and are responsive to a variety of cytokines including IL-4.

TF-1.8 cells have been transfected with the firefly luciferase gene contained in the expression vector, pPGK-puromycin-luciferase (Coombe et al, 1998, supra). The positive transfectants are cloned to produce a line with good luciferase expression. The proliferation assays are carried out in 96-well microplates suitable for such assays (Falcon). The wells are flat bottomed, with white sides and a clear bottom. Cells are washed to remove any cytokine in the growth medium and then resuspended in RPMI/5% w/v FCS. The cells are counted with a Coulter Z2 Particle Counter and Size Analyzer (Coulter Electronics, England) and routinely 2.5× $10^4$ cells are added to microplate wells that contain either no IL-4 (negative control) or various dilutions of IL-4. When the effect of anionic oligosaccharide conjugates, or other sulfated polysaccharides, is to be measured, the wells also contain various concentrations of these molecules.

The cells proliferate for 48 hours at 37° C. in a humidified atmosphere, after which the luciferase activity is measured by the addition of 50 µl of luciferase substrate buffer (50 mM Tris-HCl, pH 7.8, 15 mM $MgSO_4$, 33.3 mM DTT, 0.1 mM EDTA, 0.5 mM Na-luciferin, 0.5 mM ATP, 0.25 mM lithium Co A and 0.5% v/v Triton X-100). Immediately after the addition of the luciferase buffer the plate is assayed for luciferase activity. Light emissions are detected on a Victor 1420 Multi-label counter (Wallac, Turku, Finland).

Using this assay, the inventors demonstrated that some anionic oligosaccharide conjugates very markedly inhibit the IL-4 dependent proliferation of TF-1.8 cells whereas others are less active (Table 4).

The saccharide component of the anionic oligosaccharide conjugate seems to be important for activity. Both the size of the oligosaccharide and the underlying composition seems to be important. The linked pentasaccharides are more effective inhibitors than linked tetrasaccharides and of the linked pentasaccharides the linked sulfated maltose series was the most effective but the linked sulfated xylan pentasaccharides also displayed considerable activity. Interestingly some of the linked sulfated maltotetraose anionic oligosaccharide conjugates with small linkers (Et1 and Et2) displayed similar activity to that of the linked sulfated maltopentaoses, but those linked sulfated maltotetraoses with longer linkers had reduced activity. Thus, it appeared that a continuous presentation of sulfated residues on a maltose backbone is preferred rather than clusters of sulfated residues displayed on a maltose backbone separated by a non-sulfated, non-saccharide region. The anionic oligosaccharide conjugates with the best activity were those with Compound IDs 6-10. Of the sulfated linked xylan series the linked pentasaccharide structures were more active than the linked tetrasaccharides and on balance of these linked sulfated pentasaccharides those with a linker of size Et2 and Et3 were preferred.

dilutions of GM-CSF. The cells are cultured for 48 hours at 37° C. in a humidified atmosphere, after which the luciferase activity is measured by the addition of 50 μL of luciferase substrate buffer (50 mM Tris-HCl, pH 7.8, 15 mM $MgSO_4$, 33.3 mM DTT, 0.1 mM EDTA, 0.5 mM Na-luciferin, 0.5 mM ATP, 0.25 mM lithium Co A and 0.5% v/v Triton X-100). Immediately after the addition of the luciferase buffer the plate is assayed for luciferase activity. Light emissions are detected on a Victor 1420 Multi-label counter (Wallac, Turku, Finland). When the effect of the anionic oligosaccharide conjugates, or other sulfated polysaccharides is to be measured, the wells also contain various concentrations of these molecules as well as the GM-CSF. These experiments have indicated that concentrations of 10 μg/mL and 1 μg/mL of the anionic oligosaccharide conjugates reproducibly have no effect on the TF-1.8 cell proliferation obtained with 0.025 ng/mL of GM-CSF (Table 5).

TABLE 4

The ability of the anionic oligosaccharide conjugates to inhibit IL-4 dependent cell proliferation

| | | | % Inhibition of TF1.8 cell proliferation stimulated by IL-4 | | |
|---|---|---|---|---|---|
| ID | Persulfated oligosaccharide | Linker | Anionic oligosaccharide conjugate (2.5 μg/mL) | Anionic oligosaccharide conjugate (5 μg/mL) | Anionic oligosaccharide conjugate (10 μg/mL) |
| 1 | Maltotriose | Et1 | 0 | 34.4 ± 1.2 | |
| 2 | Maltotriose | Et2 | 24.9 ± 1.7 | 27.1 ± 3.4 | |
| 3 | Maltotriose | Et3 | 0 | 22.6 ± 1.8 | |
| 4 | Maltotriose | Et4 | 0 | 12 ± 0.7 | |
| 5 | Maltotriose | Et5 | 22.8 ± 7.2 | 10.3 ± 12.7 | |
| 6 | Maltopentaose | Et1 | 59 ± 6.6 | 74.5 ± 8.5 | 82.8 ± 0.8 |
| 7 | Maltopentaose | Et2 | 37.8 ± 4.1 | 92.9 ± 16.7 | 90.5 ± 1.6 |
| 8 | Maltopentaose | Et3 | 44.9 ± 7.7 | 58.7 ± 11.8 | |
| 9 | Maltopentaose | Et4 | 45.2 ± 3.4 | 59.3 ± 1.1 | 84.1 ± 0.8 |
| 10 | Maltopentaose | Et5 | 46.5 ± 2.4 | 57.9 ± 8.9 | 81.9 ± 1.9 |
| 11 | Maltotetraose | Et1 | 40.3 ± 7.4 | 65.6 ± 3.3 | |
| 12 | Maltotetraose | Et2 | 38.1 ± 3.3 | 63.3 ± 3.2 | 67.5 ± 0.6 |
| 13 | Maltotetraose | Et3 | 23.4 ± 3.7 | 44.4 ± 3 | |
| 14 | Maltotetraose | Et4 | 18.2 ± 6.4 | 42.0 ± 5.1 | |
| 15 | Maltotetraose | Et5 | 32.7 ± 3.9 | 41.4 ± 5.4 | |
| 66 | Chitotetraose | Et1 | 5.7 ± 11.9 | | 23.2 ± 3 |
| 67 | Chitotetraose | Et2 | 0 | | 34.4 ± 2.4 |
| 68 | Chitotetraose | Et3 | 0 | | 27.1 ± 6.6 |
| 69 | Chitotetraose | Et5 | 13.9 ± 4.8 | | 29 ± 4.8 |
| 70 | Chitopentaose | Et1 | 23 ± 11.2 | | 25.1 ± 2.1 |
| 71 | Chitopentaose | Et2 | 21.5 ± 2.8 | | 30.1 ± 4.8 |
| 72 | Chitopentaose | Et3 | 9.1 ± 3.8 | | 29.2 ± 2.7 |
| 73 | Chitopentaose | Et4 | 11.8 ± 7.2 | | 28.5 ± 4.1 |
| 74 | Chitopentaose | Et5 | 4.4 ± 1.1 | | 34.2 ± 2.3 |
| 75 | Xylotetraose | Et1 | 24.9 ± 5.1 | | 41.3 ± 1 |
| 76 | Xylotetraose | Et2 | 19.1 ± 1.6 | | 43.4 ± 5.1 |
| 77 | Xylotetraose | Et3 | 25.7 ± 8.2 | | 50.4 ± 3.1 |
| 78 | Xylotetraose | Et4 | 26.7 ± 5.6 | | 36.3 ± 3.6 |
| 79 | Xylotetraose | Et5 | 21.3 ± 2.7 | | 39.6 ± 4.1 |
| 80 | Xylopentaose | Et1 | 32.7 ± 2.8 | | 56.6 ± 3.2 |
| 81 | Xylopentaose | Et2 | 32.3 ± 4.8 | | 59.2 ± 3.1 |
| 82 | Xylopentaose | Et3 | 29.2 ± 4 | 40.3 ± 3 | 58.4 ± 2.4 |
| 83 | Xylopentaose | Et4 | 38.2 ± 7.3 | 42.5 ± 4 | 53.6 ± 4.3 |
| 84 | Xylopentaose | Et5 | 30.9 ± 3.1 | 32.6 ± 4.8 | 52.8 ± 3.5 |

Example 13

Functional Analyses of Anionic Oligosaccharide Conjugates on Cell Proliferation Targets GM-CSF and IL-2

TF-1.8 cells were derived from TF-1 cells that respond to human GM-CSF (granulocyte-macrophage colony stimulating factor). TF-1.8 cells retained their responsiveness to GM-CSF. Routinely $2.5 \times 10^4$ cells are added to microplate wells that contain either no GM-CSF (negative control) or various The murine cytotoxic T lymphocytic line (CTLL) is a subclone of T cells derived from a C57bl/6 mouse. The cells require interleukin-2 (IL-2) for growth and are used to assay for its presence in conditioned media. The cells are responsive to both murine and human IL-2. CTLL cells have been transfected with the firefly luciferase gene contained in the expression vector, pPGK-puromycin-luciferase (Coombe et al, 1998, supra). The positive transfectants are cloned to produce a line with good luciferase expression and these cells are called CTL-Luc. The proliferation assays are carried out in 96-well microplates suitable for such assays (Falcon). The wells are flat bottomed, with white sides and a clear bottom.

proteins described in the other examples means the anionic oligosaccharide conjugates of the present invention have a therapeutic potential.

TABLE 5

The ability of the various anionic oligosaccharide conjugates to inhibit cell proliferation dependent upon human GM-CSF or human IL-2

| | | | % Inhibition of cytokine stimulated cell proliferation | |
|---|---|---|---|---|
| ID | Persulfated oligosaccharide | Linker | GM-CSF 10 μg/mL (TF1.8 cells) | IL-2 10 μg/mL (CTL-luc cells) |
| 5 | Maltotriose | Et5 | | |
| 6 | Maltopentaose | Et1 | −5.7 ± 1.4 | −0.1 ± 4.2 |
| 7 | Maltopentaose | Et2 | −6.7 ± 6 | −0.2 ± 6.4 |
| 8 | Maltopentaose | Et3 | 8.7 ± 3.5 | −1.7 ± 4.4 |
| 9 | Maltopentaose | Et4 | 3.6 ± 1.7 | 1.3 ± 2.5 |
| 10 | Maltopentaose | Et5 | −1.9 ± 2 | 0.4 ± 5.8 |
| 15 | Maltotetraose | Et5 | | |
| 69 | Chitotetraose | Et5 | | |
| 70 | Chitopentaose | Et1 | −10.9 ± 7.5 | |
| 71 | Chitopentaose | Et2 | −2.4 ± 6.1 | |
| 72 | Chitopentaose | Et3 | −2 ± 5.5 | |
| 73 | Chitopentaose | Et4 | −11.8 ± 5.8 | |
| 74 | Chitopentaose | Et5 | −9.1 ± 1.1 | |
| 75 | Xylotetraose | Et1 | | |
| 79 | Xylotetraose | Et5 | | |
| 80 | Xylopentaose | Et1 | 5.2 ± 6.8 | |
| 81 | Xylopentaose | Et2 | 7.4 ± 10.3 | |
| 82 | Xylopentaose | Et3 | −0.4 ± 0.1 | |
| 83 | Xylopentaose | Et4 | −2.2 ± 2.6 | |
| 84 | Xylopentaose | Et5 | 0.3 ± 5.2 | |

Apparent slight stimulation of cell proliferation is indicated by a negative value.

Cells are washed to remove any cytokine in the growth medium and then resuspended in RPMI/5% w/v FCS. The cells are counted with a Coulter Z2 Particle Counter and Size Analyzer (Coulter Electronics, England) and routinely 1.6× $10^4$ cells are added to microplate wells that contain either no recombinant human IL-2 (rhIL-2) (negative control) or various dilutions of rhIL-2. When the effect of anionic oligosaccharide conjugates, or other sulfated polysaccharides is to be measured, the wells also contain various concentrations of these molecules.

The CTL-Luc cells proliferate for 24 hours at 37° C. in a humidified atmosphere, after which the luciferase activity is measured by the addition of 50 μL of luciferase substrate buffer (50 mM Tris-HCl, pH 7.8, 15 mM $MgSO_4$, 33.3 mM DTT, 0.1 mM EDTA, 0.5 mM Na-luciferin, 0.5 mM ATP, 0.25 mM lithium Co A and 0.5% v/v Triton X-100). Immediately after the addition of the luciferase buffer the plate is assayed for luciferase activity. Light emissions are detected on a Victor 1420 Multi-label counter (Wallac, Turku, Finland). Experiments in which the CTL-Luc cells are cultured in the presence of either 10 μg/mL or 1 μg/mL of anionic oligosaccharide conjugates reproducibly have no effect on the proliferation of CTL-Luc cells obtained with 1.25 ng/mL of rhIL-2. (Table 5). The results of these experiments with the IL-2 and GM-CSF responsive cell lines suggest that none of the anionic oligosaccharide conjugates tested interact with these cytokines in a manner that affects their proliferative activity. The results of these experiments also suggest that the tested anionic oligosaccharide conjugates are not toxic to cytokine dependent lymphocytic cell lines. These examples show that while the tested anionic oligosaccharide conjugates of the present invention bind to cytokines this doesn't necessarily invoke any therapeutic potential for the tested anionic oligosaccharide conjugates. In contrast binding to the target Example 14

Functional Analyses of Anionic Oligosaccharide Conjugates on the COPD Target Protein, Human Leukocyte Elastase.

Elastase is a protein that is a potential target for the treatment of COPD. Elastase assays were performed in 96-well plastic microplates for easy quantification by the fluorescent plate reader. Human leukocyte elastase (5 nM/well) was incubated in the presence of rabsence of sulfated polysaccharides, with the fluorogenic substrate MeOSuc-Ala-Ala-Pro-Val-amido-methylcoumarin (20 μM/well) in a sodium phosphate buffer, pH 7.4. The mixture was incubated at 37° C. for 60 minutes before the reaction was stopped by the addition of 10 μL/well of 250 nM acetic acid and the mixture transferred to a 96-well microplate with fluorescence being measured using an excitation wavelength of 355 nm and an emission wavelength of 460 nm. Various concentrations of inhibitors were used to allow the calculation of the concentration of anionic oligosaccharide conjugate required to inhibit enzyme activity by 50% ($IC_{50}$). These data indicated that the different anionic oligosaccharide conjugates inhibited elastase activity to differing degrees, but the structure comprising the sulfated chitopentaose joined by the various sized Et linkers were the most effective having an $IC_{50}$ in this assay of approximately between 32-70 nM, with the structures comprising the smallest linkers Et1 and Et2 having the best activity. Thus, the En linked sulfated chitopentaose and the Et2 linked sulfated chitopentaose had $IC_{50}$ of 32 and 34 nM. The best of the linked sulfated maltopentaoses was ID 10 with an $IC_{50}$ of 48 nM. The linked xylopentaose series were not very effective inhibitors of elastase activity. In this assay heparin has an $IC_{50}$ of approximately 200 nM (Table 6).

TABLE 6

The ability of the various anionic oligosaccharide conjugates to inhibit the activity of human leukocyte elastase

| ID | Persulfated oligosaccharide | Linker | Inhibition of Elastase activity IC$_{50}$ nM |
|---|---|---|---|
| 1 | Maltotriose | Et1 | 2200 |
| 2 | Maltotriose | Et2 | |
| 3 | Maltotriose | Et3 | 667 |
| 4 | Maltotriose | Et4 | |
| 5 | Maltotriose | Et5 | |
| 6 | Maltopentaose | Et1 | |
| 7 | Maltopentaose | Et2 | 100 |
| 8 | Maltopentaose | Et3 | 222 |
| 9 | Maltopentaose | Et4 | 223 |
| 10 | Maltopentaose | Et5 | 48 |
| 11 | Maltotetraose | Et1 | 480 |
| 12 | Maltotetraose | Et2 | 500 |
| 13 | Maltotetraose | Et3 | 520 |
| 14 | Maltotetraose | Et4 | 1100 |
| 15 | Maltotetraose | Et5 | 1250 |
| 66 | Chitotetraose | Et1 | 140 |
| 67 | Chitotetraose | Et2 | |
| 68 | Chitotetraose | Et3 | 240 |
| 69 | Chitotetraose | Et5 | 180 |
| 70 | Chitopentaose | Et1 | 32 |
| 71 | Chitopentaose | Ef2 | 34 |
| 72 | Chitopentaose | Et3 | 70 |
| 73 | Chitopentaose | Et4 | 55 |
| 74 | Chitopentaose | Et5 | 70 |
| 75 | Xylotetraose | Et1 | 290 |
| 76 | Xylotetraose | Et2 | 460 |
| 77 | Xylotetraose | Et3 | 540 |
| 78 | Xylotetraose | Et4 | 450 |
| 79 | Xylotetraose | Et5 | 280 |
| 80 | Xylopentaose | Et1 | 480 |
| 81 | Xylopentaose | Et2 | 470 |
| 82 | Xylopentaose | Et3 | 410 |
| 83 | Xylopentaose | Et4 | 420 |
| 84 | Xylopentaose | Et5 | 300 |

Example 15

Functional Analyses of Anionic Oligosaccharide Conjugates on Chemokines Implicated in Inflammation Associated with COPD.

Chemokines known to play an important role in mediating the inflammation associated with COPD include IL-8, MCP-1 and MIP-1α (Barnes 2004, supra). Various Anionic oligosaccharide conjugates were shown to block cell migration triggered by IL-8. These experiments were performed using DMSO treated human promyelocytic HL-60 cells. These cells were derived from a patient with acute promyelocytic leukemia. The cells were treated with DMSO (1.2%) for 4 days before being used in the experiments. The chemotaxis assays were performed in 96-well Costar chemotaxis plates consisting of a bottom chamber to which was added the human IL-8 (+/− inhibitor) and then cells in RPMI and 1% v/v FCS were added to a top chamber and the plate was incubated at 37° C. for 1 hour to allow cells to move from the top chamber into the bottom. The number of cells migrating into the bottom chamber was quantified by labeling with AQUEOUS ONE (20 µL/well) for 1.75 hours before absorbance at 490 nm is read. IL-8 was used at a final concentration of 20 ng/mL and the anionic oligosaccharide conjugate inhibitors were used at either 10 or 50 µg/mL, % inhibition data are shown for 50 µg/mL (Table 7).

To examine whether the various anionic oligosaccharide conjugates were effective inhibitors of the chemokine MCP-1 the human monocytic cell line THP-1 was used. These cells were originally derived from the peripheral blood of a patient with acute monocytic leukaemia. The assay was very similar to that described above, except that the cells were placed in 1% foetal calf serum for 20 hour prior to the assay commencing. The chemotaxis assays were performed in 96-well Costar chemotaxis plates and human MCP-1 (+/− inhibitor) was added to the bottom chamber and the THP-1 cells in RPMI/1% FCS were added to the top chamber and the plate was incubated at 37° C. for 2.5 hour to allow cells to move from the top chamber into the bottom. The number of cells migrating into the bottom chamber was quantified by labeling with AQUEOUS ONE (30 µL/well) for 3.5 hours before absorbance at 490 nm is read. MCP-1 was used at a final concentration of 10 ng/mL and the various anionic oligosaccharide conjugate inhibitors were used at either 10 or 50 µg/mL; % inhibition data are shown for 50 µg/mL (Table 7).

DMSO treated U937 cells were used to examine the cell migration in response to MIP-1α. U937 cells are a promonocytic human cell line originally derived from the pleural effusion of a patient with histiocytic lymphoma. These cells were treated with DMSO (1.2%) for 4 days before being used in chemotaxis experiments. The chemotaxis assays were performed in 96-well Costar chemotaxis plates and human MIP-1α (+/− inhibitor) was added to the bottom chamber and the DMSO treated U937 cells in RPMI/HEPES were added to the top chamber and the plate was incubated at 37° C. for 1.5 hours to allow cells to move from the top chamber into the bottom. The number of cells migrating into the bottom chamber was quantified by labeling with AQUEOUS ONE (30 µL/well) for 1 hour before absorbance at 490 nm is read. MIP-1α was used at a final concentration of 40 ng/mL and the various anionic oligosaccharide conjugate inhibitors were used at 10 and 50 µg/mL; % inhibition data are shown for 50 µg/mL (Table 7).

The data indicate that a different suite of anionic oligosaccharide conjugates inhibits each of the chemokines tested and it was not obvious a priori which anionic oligosaccharide conjugates would block chemokine function. MCP-1 is the chemokine whose function is best blocked by the anionic oligosaccharide conjugates and the linked sulfated maltopentaose series are particularly effective in this regard. The size of the linker appears less important than the length of the oligosaccharide in the conjugate, as both a linked sulfated maltotriose and various linked sulfated maltotetraoses are less effective inhibitors than the equivalent anionic oligosaccharide conjugate for which the oligosaccharide is a sulfated maltopentaose. Other anionic oligosaccharide conjugates that show good inhibitory activity are the linked sulfated xylans that are composed of a short linker (Et1). It appears that a continuous presentation of sulfates on the xylan backbone without a stretch lacking in sulfate is what is required for activity here, thus the size of each individual oligosaccharide in the conjugate is of less importance.

In contrast to the situation with MCP-1, IL-8 is not inhibited to any degree by the linked sulfated maltose series, but it is blocked by anionic oligosaccharide conjugates of the linked sulfated xylan series (Table 7). Like the situation with MCP-1 those linked sulfated xylans composed of a short linker (Et1) are the most effective inhibitors of IL-8 activity. Thus, a continuous presentation of sulfates on the xylan backbone without a stretch lacking in sulfate is what is required for activity and the size of each individual oligosaccharide in the conjugate is of less importance.

Very few of the anionic oligosaccharide conjugates inhibited the functional activity of MIP-1α and those that inhibited did so weakly. The anionic oligosaccharide conjugates that were most effective comprised the linked sulfated maltopentaoses. The length of the linker appeared to be of less importance than the length of the oligosaccharide (Table 7).

TABLE 7

The ability of the various anionic oligosaccharide conjugates to inhibit cell migration induced by chemokines with a role in COPD

| ID | Persulfated oligosaccharide | Linker | % Inhibition of chemokine stimulated cell migration by 50 µg/mL anionic oligosaccharide conjugate | | |
|---|---|---|---|---|---|
| | | | MCP-1 | IL-8 | MIP-1α |
| 5 | Maltotriose | Et5 | 72.6 ± 1 | 52.3 ± 3.5 | −10 ± 0.5 |
| 6 | Maltopentaose | Et1 | | | |
| 7 | Maltopentaose | Et2 | 105 ± 3.4 | 32.9 ± 2.3 | 23.5 ± 7.1 |
| 8 | Maltopentaose | Et3 | | | |
| 9 | Maltopentaose | Et4 | 107.9 ± 2.8 | 26.6 ± 4.7 | 26.5 ± 6.6 |
| 10 | Maltopentaose | Et5 | 92.6 ± 0.3 | 26.6 ± 4.7 | 26.1 ± 2.5 |
| 11 | Maltotetraose | Et1 | | | |
| 12 | Maltotetraose | Et2 | | | |
| 13 | Maltotetraose | Et3 | 77.6 ± 1 | 36.7 ± 6 | −33 ± 6.7 |
| 14 | Maltotetraose | Et4 | 71.7 ± 4.2 | 23.9 ± 1.3 | −6.8 ± 0.8 |
| 15 | Maltotetraose | Et5 | 85.7 ± 1.7 | | 30.2 ± 10.3 |
| 66 | Chitotetraose | Et1 | | | |
| 67 | Chitotetraose | Et2 | 19.4 ± 0.4 | 26.2 ± 6.1 | −8.5 ± 11.1 |
| 68 | Chitotetraose | Et3 | | | |
| 69 | Chitotetraose | Et5 | | | |
| 70 | Chitopentaose | Et1 | 14.1 ± 1.8 | 31 ± 1.3 | 5.9 ± 5.1 |
| 74 | Chitopentaose | Et5 | | | |
| 75 | Xylotetraose | Et1 | 66.6 ± 1.6 | 89.6 ± 9.5 | 1.3 ± 2.2 |
| 79 | Xylotetraose | Et5 | | | |
| 80 | Xylopentaose | Et1 | 62.4 ± 1.1 | 94.5 ± 11.8 | −11.4 ± 6 |
| 81 | Xylopentaose | Et2 | | | |
| 82 | Xylopentaose | Et3 | 57 ± 0.2 | 30.5 ± 2.7 | −31.2 ± 4.9 |
| 83 | Xylopentaose | Et4 | | | |
| 84 | Xylopentaose | Et5 | 57.5 ± 1.7 | 52.2 ± 3.7 | −38.2 ± 1.1 |

Apparent slight stimulation of cell migration is indicated by a negative value.

Example 16

Functional Analyses of Two Anionic Oligosaccharide Conjugates on the Inhibition of Leukocyte Infiltration in an Allergic Rhinitis Animal Model An allergic rhinitis model in the guinea pig was used. The guinea pigs are sensitized to ovalbumin (OVA) twice (on days 0 and 7) by an intraperitoneal injection of 0.5 mL saline containing 100 mg Al(OH)$_3$ and 2 µg OVA. Three weeks after the last sensitization, animals are anaesthetized and the exposure of the nasal cavity to allergen is performed by dropping OVA solution at 20 mg/mL into bilateral nasal cavities. For the negative control the animals receive sensitization and challenge with saline. The animals are pretreated with either vehicle or drug (anionic oligosaccharide conjugates or Budesonide) 30 min prior to intranasal instillation of OVA. Vehicle or drugs are administered, 25 µl-50 µl/nostril. A comparison of the anionic oligosaccharide conjugates with Budesonide, as the reference compound, is included. Animals are terminated and all parameters measured eight hours after the provocation.

The nasal mucosal barrier permeability is assessed by measuring the leakage of protein-rich and non-sieved plasma into the nasal cavities. The amount of extravasated plasma is indicated as nasal lavage levels of total protein or albumin. Nasal lavage fluid is collected by gently rinsing the nasal cavities with phosphate buffered saline. The cells in this fluid are centrifuged and resuspended in phosphate buffered saline and counted using a semiautomated haematology analyzer. The cell composition of the nasal lavage is determined after a cytospin and staining with May Grynwald Giemsa.

Figure 3:
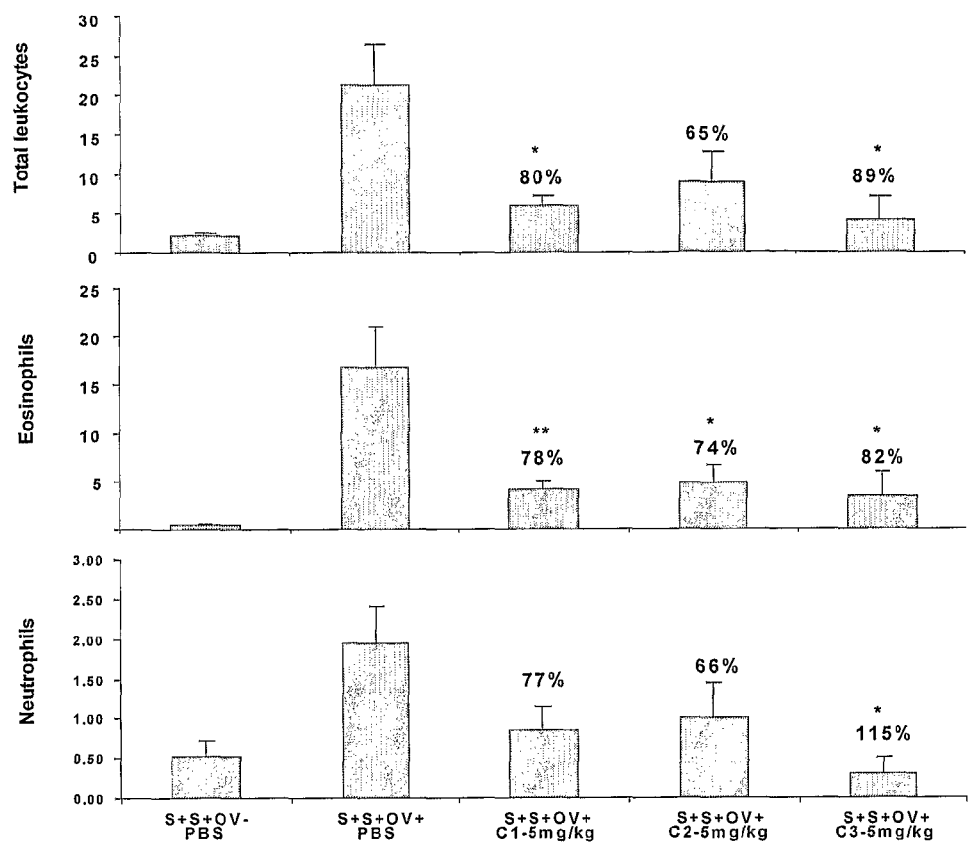
FIG. 3 shows the effects of 5 mg/kg compounds on leukocytes in nasal lavage fluid collected 8 hours after challenge in an allergic rhinitis model in guinea pigs. The compounds are, C1: pentosan, C2: (Maltopentaose)-(Et2)-(Maltopentaose) and C3: (Maltopentaose)-Et4-(Maltopentaose).

The data indicate that levels of plasma exudation to the nasal cavity were significantly increased 8 hours after intranasal challenge with OVA. The two Anionic oligosaccharide conjugates significantly reduced the protein content of the nasal lavage fluid indicating a reduction in plasma exudation with this drug. Tested were the Et2 linked sulfated maltopentaose (ID 7) and the Et4 linked sulfated maltopentaose (ID 9) and of these the former was most effective; % inhibitions obtained were respectively 91.4% and 51.5% when used at a concentration of 5 mg/kg. An assessment of leukocyte infiltration into the nasal lavage fluid indicated an increased leukocyte count over that seen with animals sensitized with saline, however the two anionic oligosaccharide conjugates inhibited leukocyte infiltration at the concentration tested with one being more effective than the other (FIG. 3). The most marked leukocytes in the nasal lavage are eosinophils with some evidence of neutrophil infiltration, the levels of other cell types: basophils, lymphocytes, monocytes and nasal epithelial cells are low and not significantly different from that seen in animals sensitized with saline. Animals receiving the corticosteroid Budesonide had a marked decrease in plasma exudation in the nasal lavage and also a marked decrease in the total white cell numbers in the nasal lavage fluid, the most pronounced decrease being in the numbers of eosinophils. The anionic oligosaccharide conjugates similarly markedly reduced the cellular infiltrate into the nasal lavage fluid. Notably one of the anionic oligosaccharide conjugates, ID 9 (Et4 linked maltopentaose) was particularly effective at blocking not only eosinophil infiltration but also neutrophil infiltration whereas the other anionic oligosaccharide conjugate with a shorter linker (Et2 linked maltopentaose, ID 7) behaved like the corticosteroid and only blocked eosinophils (FIG. 3).

Example 17

Functional Analysis of an Anionic Oligosaccharide Conjugate in an Asthma Animal Model A guinea pig model of asthma was used. In this model guinea pigs (9-10 per group) were sensitized to OVA by two intraperitoneal injections of 0.5 mL saline containing 20 mg Al(OH)$_3$ and 20 µg OVA. The sensitizations are performed on days 0 and 7. Three weeks after the last sensitization, animals were pre-treated with either vehicle or drugs 30 min prior to inhalation of OVA (at 10 mg/mL) for 6 min (allergen challenge). For the negative control, animals received either sensitization and challenge with saline or sensitization with saline and challenge with OVA. Animals were terminated and all parameters measured 8 hours after the provocation. Vehicle or drugs were administered intra-tracheally, 1 mL/kg body weight, 30 min before the intra-tracheal challenge with OVA. The vehicle for the drugs (anionic oligosaccharide conjugates and budesonide) was saline. Budesonide as the reference compound was dissolved in the vehicle at concentrations of 1 mg/mL. To measure airway resistance ($R_L$) and lung compliance ($C_{dyn}$) bronchoconstriction was evoked with aerosolized methacholine (3 mg/mL, 10 mg/mL and 30 mg/mL). The difference between baseline readings and that obtained after methacholine were used to calculate $C_{dyn}$ and $R_L$. Bronchoalveolar lavage (BAL) was performed immediately after the lung function measurements. BAL was analysed for protein content (as a measure of leakage) and leukocyte number, differential cell counts were performed to indicate what subsets of leukocytes the drugs best affected.

The lung function measurements (Table 8) clearly indicate that the anionic oligosaccharide conjugate ID 9 (Et4 linked sulfated maltopentaose) inhibited the development of both Cdyn and RL. The anionic oligosaccharide conjugate ID 9 at the highest concentration restored Cdyn and RL close to that seen with the negative control, and there is evidence of a dose response for anionic oligosaccharide conjugate ID 9. The effectiveness of the anionic oligosaccharide conjugate was at least that of the reference compound, the corticosteroid budesonide (ignoring budesonide 2.5 mg/kg 10 MCh, as one animal in this group gave a reading 10-fold out, which biased the mean). Thus, the anionic oligosaccharide conjugate ID 9 showed efficacy on lung function measurements in this guinea pig model even when used at low concentrations.

TABLE 8

Airway Hyperreactivity (AHR) Summary - AHR data expressed as % inhibition from that of the positive control for $R_L$ and % increase from that of the positive control for $C_{dyn}$

| Compound | $R_L$ | | $C_{dyn}$ | |
|---|---|---|---|---|
| | MCh (10 mg/mL) | MCh (30 mg/mL) | MCh (10 mg/mL) | MCh (30 mg/mL) |
| Budesonide 0.1 mg/kg | 86.5%** | 105%** | 97.2%** | 116.2%** |
| Budesonide 2.5 mg/kg | −89.4% | 98.9%** | 19.7% | 70.9%** |
| ID 9 0.1 mg/kg | 75.3%* | 84.4%** | 76.6%** | 90%** |
| ID 9 2.5 mg/kg | 80.5%** | 99.5%** | 68.7%* | 128.4%** |

The data are shown for two different methacholine concentrations, 10 mg/kg and 30 mg/kg. Data obtained with methacholine at 3 mg/kg was not significantly different from baseline levels in any of the groups tested including the positive control. The $R_L$ increases with an allergic reaction whereas elasticity or $C_{dyn}$ decreases, thus in the table the values given are % decrease from the positive control for $R_L$ but % increase from the positive control for $C_{dyn}$.
**significantly different at P < 0.01
*significantly different at P < 0.05

Figure 4:
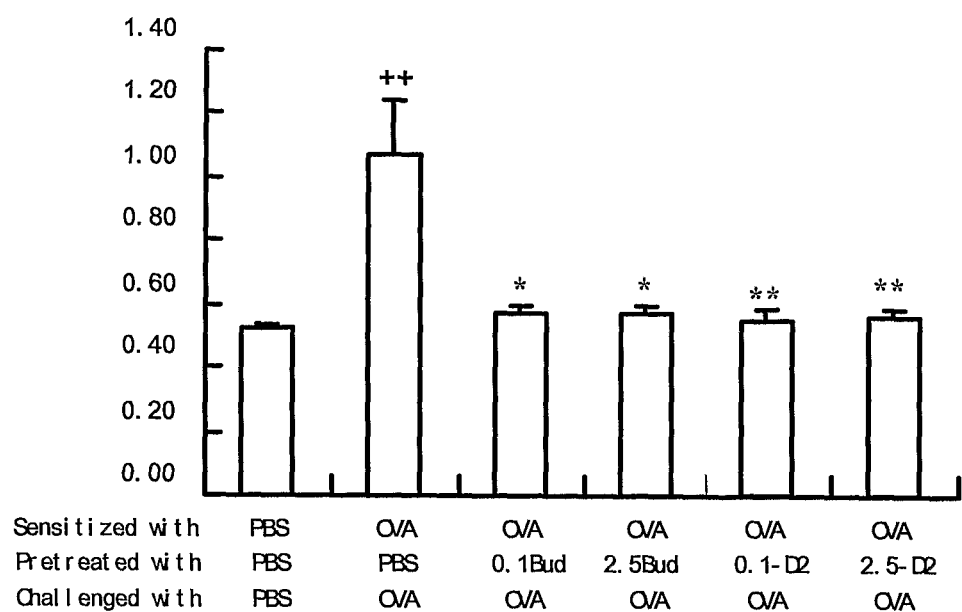
FIG. 4 shows the effects of Budesonide and the anionic oligosaccharide conjugate at different doses on antigen-increased total protein content in BAL fluid (mg/mL) from allergic/asthmatic guinea pigs.
Figure 5:
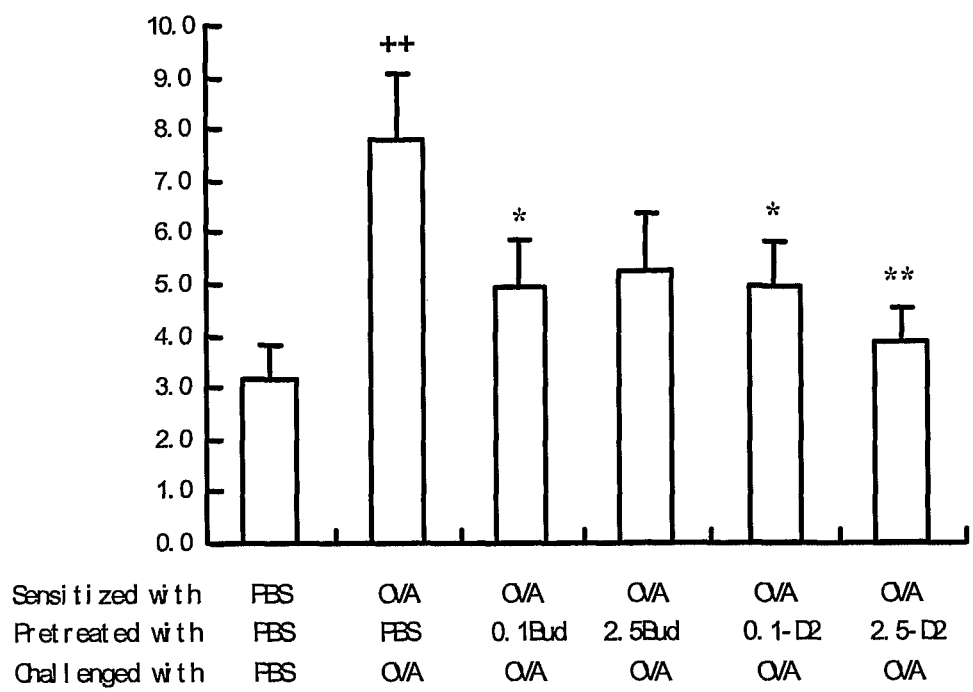
FIG. 5 shows the effects of budesonide and the anionic oligosaccharide conjugate at different doses on antigen-increased total leukocyte influx in BAL fluid ($\times 10^7$/mL) from allergic/asthmatic guinea pigs.
Figure 6:
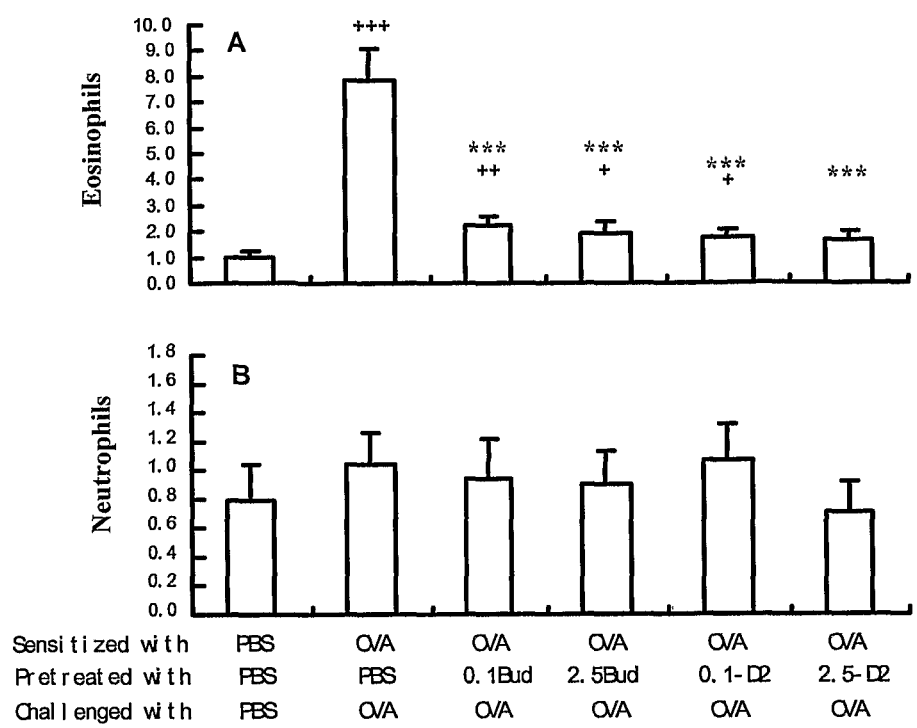
FIG. 6 shows the effects of budesonide and the anionic oligosaccharide conjugate at different doses on antigen-increased eosinophil and neutrophil influx in BAL fluid ($\times 10^7$/mL)

The anionic oligosaccharide conjugate ID 9 very effectively inhibits the elevated protein content of BAL as a result of antigen induced protein leakage, even at 0.1 mg/kg (FIG. 4). The efficacy of the anionic oligosaccharide conjugate was comparable to that seen with budesonide. Similarly, pretreatment the anionic oligosaccharide conjugate ID 9 or budesonide at 0.1 mg/kg significantly inhibited the OVA induced leukocyte influx (inhibition of 62% and 76% respectively). Pretreatment with the anionic oligosaccharide conjugate ID 9 at 2.5 mg/kg was more effective at inhibiting leukocyte influx (inhibition of 85%), whereas budesonide at 2.5 mg/kg did not significantly inhibit leukocyte influx (FIG. 5). A differential cell count of the leukocytes in the BAL revealed that the number of eosinophils were significantly higher in OVA sensitized and challenged animals compared to the negative control animals and that eosinophils were primarily the cell type that was inhibited (FIG. 6). Both budesonide and the anionic oligosaccharide conjugate ID 9 significantly inhibited eosinophil influx, with inhibitory effects between 80 and 90%. There was no significant difference in the number of neutrophils between the positive and negative controls and no difference when pretreated with any of the drugs. Similarly, there was no significant difference in the number of basophils between the positive and negative controls and no difference when pretreated with any of the drugs (data not shown). The number of macrophages in the BAL fluid was significantly higher in OVA sensitized and challenged animals compared to negative control animals. Pretreatment with the drugs did not significantly reduce the level of macrophages although some of the treatments tended to produce reduced levels (data not shown).

In conclusion, at the concentrations tested the anionic oligosaccharide conjugate ID 9 was at least as effective at inhibiting (1) the protein content of the BAL, (2) airway hyperreactivity, and (3) the leukocyte, and particularly the eosinophil influx into the BAL, as the reference corticosteroid budesonide in this guinea pig model of allergic asthma.

Example 18

Functional Analysis of an Anionic Oligosaccharide Conjugate in a COPD Animal Model A mouse model of emphysema was used. Acute or chronic exposure of mice to cigarette smoke lead to lung responses that in part mimic the inflammatory and structural changes observed in COPD. In this model male C57Bl/6J mice are subjected to acute or chronic smoke exposure, with normal room air being the control situation. In the acute study mice were exposed to either room air or to the smoke of five cigarettes (approximately 12 mg of tar and 0.9 mg of nicotine) for 20 minutes. In the chronic study mice were exposed to either room air or to the smoke of three cigarettes/day for 5 days/week for 6 months. The 4 groups of mice were then further divided so that mice within each group also received various anionic oligosaccharide conjugates via an inhaled route.

In the acute exposure groups of mice anionic oligosaccharide conjugates were given 30 minutes before exposure to cigarette smoke. Assessment of the efficacy of the drug for mice in the acute exposure groups involved assessment of trolox equivalent anti-oxidant capacity of the bronchoalveolar lavage fluid (BALF) at the end of smoke exposure. The BALF was examined for cytokines and chemokines that are associated with an inflammatory response. The levels of these agents were determined at 4 hours after exposure and at 24 hours after cigarette smoke exposure. A range of cytokines and chemokines was measured. These included: IL-1α, IL-1β, IL-2, IL-3, IL-4, IL-5, IL-6, IL-10, IL-12, RANTES, MIP-1α, cytokine-induced neutrophil chemoattractant (KC), TNF-α and IFN-γ). A differential cell count of the cells in the BALF was also determined. The results of this study indicated that an anionic oligosaccharide conjugate (ID 9) decreased the cellular infiltrate into BALF of animals exposed to cigarette smoke, in particular the numbers of neutrophils were significantly attenuated in those animals exposed to cigarette smoke and which also received the anionic oligosaccharide conjugate.

The animals in the chronic study received the anionic oligosaccharide conjugates (including ID 9) once a day for the duration of the experiment. At the completion of the experiment animals were killed and the lungs fixed intratracheally with formalin (5%) and lung volume was measured by water displacement. The lung tissue was prepared for histochemistry and immunohistochemistry, the lung tissues being stained for hematoxylin-eosin and/or periodic acid-Schiff or with antibodies to the macrophage marker Mac-3. The level of desmosine in the lung tissue was also determined. Desmosine is an elastin-specific imino acid; the assessment of desmosine in the lung is taken as an indicator of the lung elastin content. A decline in desmosine content is evidence that the emphysematous changes are associated with proteolysis and matrix breakdown. Collectively the results of this study indicated anionic oligosaccharide conjugates and in particular ID 9 could act as anti-inflammatory agents in this COPD model.

Example 19

Functional Analysis of an Anionic Oligosaccharide Conjugate in an ARDS Animal Model A rat model of acute lung injury and ADRS was used (Jansson, *Lung* 182:1-9, 2004). The model is based on the understanding that endotoxin found in common pathogens (e.g. bacteria) can lead to the development of ARDS, septic shock and multiple organ dysfunction syndrome in the clinical situation. Lipopolysaccharide (LPS), a component of the outer membrane of gram-negative bacteria is the prototypical example of endotoxin and exposure of the respiratory tract of rats to LPS can be used as a model of acute lung inflammation and ARDS. In this rat model the LPS causes increased infiltration of inflammatory cells, production of inflammatory mediators and tissue edema all of which are characteristic of acute lung inflammation and ARDS.

In this model Wister female rats were anesthetized and LPS dissolved in saline at a range of concentrations including 5, 50 and 500 µg/mL was intratracheally administered at a volume of 1 mL/kg body weight using a modified cannula. Animals received the same volume of saline and manipulations as controls. Animals were terminated 4 and 8 hours after administration of LPS. The animals receiving the anionic oligosaccharide conjugates were intra-tracheally instilled with the anionic oligosaccharide conjugates or with saline 30 minutes before administration of LPS. The concentrations used were 0.5 mg/kg and 2.5 mg/kg.

Excised lung gas volume (ELGV) is measured by Archimedes' principle and is based on the stable amount of air trapped within the excised lungs at a transpulmonary pressure of 0 cmH$_2$O. Animals for ELGV measurements were intraperitoneally injected with 0.1-0.2 mL of pentobarbitone sodium (50 mg/kg). After the chest was opened and the heart removed, the trachea was exposed and ligated with a 3-0 suture. The lungs were harvested and carefully trimmed of non-pulmonary tissue. A density determination kit (P3000, Mettler-Toledo GmbH, Sweden) and optional density determination software for the balance were used on the basis of the principle that every solid body immersed in fluid loses weight, and is expressed as g/cm$^3$. The system was set to zero to exclude the liquid density and balancing the bracket weights, tissue weights outside the beaker, and tissue buoyancy within the liquid. ELGV is determined by the difference between bracket weight and lung buoyancy in the liquid. Lung tissue edema was indicated by increased lung weight. Indication of lung tissue edema was calculated by the difference between lung tissue weight outside the beaker and bracket weight. The lung tissue density was determined by the ratio of the lung weight (difference between lung tissue weight outside the beaker and holder weight) and the air volume within the lung (ELGV).

BAL fluid was also collected. The left lung was intra-tracheally lavaged with two injections of 3 mL PBS after measurement of ELGV. The BAL fluid, collected into plastic tubes on ice, was centrifuged at 1,000 rpm, 4° C. for 10 min. The supernatant was stored at −80° C. until further analysis. The cell pellet was resuspended in PBS for counting total leukocyte number using a 15-parameter, semiautomated hematology analyser (Sysmex F820, TOA Medical Electronics Co. Kobe, Japan). Cell differentiation was counted on cytospin preparations stained with May Grunwald Giemsa. The levels of IL-1β, IL-6, TNF-α, IL-8 and MCP-1 in the BAL fluid were determined using enzyme-linked immunoadsorbent assay (ELISA) kits.

In this model in the positive control animals there was clear evidence of increased lung weights with increasing LPS concentration. There is also evidence of a rapid recruitment of neutrophils followed by the production and release of proinflammatory cytokines and chemokines (IL-1β, IL-6, TNF-α, IL-8 and MCP-1). In the animals given the anionic oligosaccharide conjugates the lung weights were restored to that of the negative controls, level of neutrophil infiltration was markedly decreased, as was the concentration of the various inflammatory mediators. Although the levels of the inflammatory mediators were not totally restored to that of the negative control, inhibition of neutrophil infiltration by the anionic oligosaccharide conjugates and in particular by anionic oligosaccharide conjugate ID 9 was marked. It is likely that the LPS activated resident macrophages in the lung mucosa and alveoli causing them to secrete a proportion of these inflammatory mediators. However, as our earlier data indicated that the anionic oligosaccharide conjugates are effective inhibitors of the biological activity of these mediators it is likely that blocking the biological activity of these chemokines reduced neutrophil infiltration and further mediator release by these cells. Moreover, the weights of the lungs when animals were treated with the anionic oligosaccharide conjugates indicate that these compounds were very effective inhibitors of edema.

Example 20

Functional Analyses of Anionic Oligosaccharide Conjugates in an Anaphylaxis Animal Model Guinea-pig anaphylaxis has for many years been considered the classical example of anaphylaxis, in contrast to other species (e.g. mice) that completely lack anaphylactic responses after allergen inhalation. Anaphylactic shock is believed to be due to liberation of histamine with subsequent contraction of smooth muscle after the inhalation of antigen into the airway and lungs. Contraction of the bronchial musculature completely shuts off the alveoli and prevents exhalation of air, and the animals die of asphyxia. In guinea-pigs allergen doses that are high enough to produce a significant late-phase responses (i.e. cellular eosinophilia, late phase exudation) inevitably also give rise to prior strong acute reactions that are so intense that some animals may die in acute airway constriction.

In this model the guinea pigs were sensitized to ovalbumin (OVA) twice (on days 0 and 7) by an intraperitoneal injection of 0.5 mL saline containing 100 mg Al(OH)$_3$ and 2 µg OVA. Three weeks after the last sensitization, animals were anaesthetized and the exposure of the nasal cavity to allergen was performed by dropping OVA solution at 2 mg/mL into bilateral nasal cavities (20 µl per nasal cavity). For the negative control the animals received sensitization and challenge with saline. The animals are pretreated with either vehicle or drug (anionic oligosaccharide conjugates or Budesonide) 30 min prior to intranasal instillation of OVA. Vehicle or drugs are administered, 25 µl-50 µl/nostril. A comparison of the anionic oligosaccharide conjugates with Budesonide, as the reference compound, is included. In this study Budesonide at 0.65 mg/kg was not effective at preventing anaphylaxis as 70% of the animals in this group died by acute airway constriction. In contrast, the anionic oligosaccharide conjugate, ID 9, when used at 5 mg/kg was twice as effective as Budesonide (at 0.65 mg/kg) at inhibiting anaphylaxis as only 35% of the animals died (3/8); similarly, the anionic oligosaccharide conjugate, ID 7, when used at 5 mg/kg also inhibited anaphylaxis as only 27% of the animals died (3/11), whereas with Budesonide 70% (7/10) animals died.

A mouse model of anaphylaxis was also used. Freshly ground whole peanut was used as the antigen. Mice were sensitized by means of intragastric gavage with 5 mg (equivalent to 1 mg of peanut protein) or 25 mg (equivalent to 5 mg of peanut protein) per mouse of ground whole peanut together with 10 µg per mouse of cholera toxin on day 0 and again on day 7. Three weeks after the initial sensitization, mice were fasted overnight and challenged with intragastric gavage with crude peanut extract of 10 mg per mouse in two doses at 30- to 40-minute intervals. Mice surviving the first challenge were rechallenged at week 5. Drugs (anionic oligosaccharide conjugates) dissolved in PBS were administered by intravenous injection into the tail vein 15 min prior to the second challenge. Cholera toxin sham-sensitized mice and naïve mice were challenged in the same manner. To monitor serum IgE antibody responses, tail vein blood was obtained at weekly intervals after initial sensitization. Levels of peanut-specific IgE were measured by using ELISA. Anaphylactic symptoms were evaluated for 30 to 40 minutes after the second challenge dose by using the following scoring system: 0, no symptoms; 1, scratching and rubbing around the nose and head; 2, puffiness around the eyes and mouth, diarrhea, pilar erecti, reduced activity, and/or decreased activity with increased respiratory rate; 3, wheezing, labored respiration, and cyanosis around the mouth and the tail; 4, no activity after prodding or tremor and convulsion; 5, death. To determine plasma histamine levels, blood was collected 30 minutes after the second intragastric gavage challenge. Histamine levels were determined using an enzyme immunoassay kit. Mast cell degranulation during systemic anaphylaxis was assessed by examination of ear samples collected immediately after anaphylactic death or 40 minutes after challenge from surviving mice. Tissues were fixed in 10% neutral-buffered formalin, and paraffin sections were stained with toluidine blue or Giemsa stain. A degranulated mast cell was defined as a toluidine blue- or Giemsa-positive cell with 5 or more distinctly stained granules completely outside of the cell. The severity of the anaphylactic response was significantly inhibited by the administration of the anionic oligosaccharide conjugate drugs as assessed by the symptom scoring system, despite the levels of peanut-specific IgE indicating the animals were allergic to the peanut allergen. In addition, the levels of histamine were lower in those animals receiving the anionic oligosaccharide conjugate drugs, suggesting these drugs scavenge histamine.

A porcine model of non-allergic anaphylaxis (i.e. not mediated by IgE and previously called anaphylactoid shock) was also used. Non-allergic anaphylaxis occurs when mast cells and basophils are activated directly by a process that does not require membrane cross-linking of FcεRI (El-Shanawany et al., *Clin. Exp. Immunol.* 153:1-9, 2008). Experimentally this can be induced by intravenous calcium ionophore A23187 (Heflin et al., *Ann. Emergency Med.* 48: 190-193, 2006). This calcium ionophore is known to trigger the rapid degranulation of mast cells and basophils in vitro. In this model pigs received an intravenous injection of A23187 (5 mg/kg). The animals were sedated and then anesthetized and arterial lines were placed to permit monitoring of mean arterial pressure and for phlebotomy. Initially, before injection, baseline arterial pressure and pulse were measured and a blood sample was drawn to obtain baseline histamine and tryptase levels. The presence of hypotension and cutaneous flushing were taken as the clinical determinants of shock and this occurred approximately 1 min after injection. At the onset of shock (>20% decrease in mean arterial blood pressure) animals received either intravenous normal saline (40 ml/kg), intravenous diphenhydramine (1 mg/kg) plus epinephrine (0.01 mg/kg), or the anionic oligosaccharide conjugate drugs ID 9 or ID 7. Reversal of shock was monitored and the time taken to return to a baseline measure was determined. Histamine and tryptase levels were determined using an ELISA method. The data indicated that histamine and tryptase levels rose significantly following injection of A23187 and the mean arterial blood pressure fell markedly. Treatment with the anionic oligosaccharide conjugate drugs increased arterial blood pressure in much the same way as the diphenhydramine and epinephrine standard therapy and in all these treatment groups the reversal of anaphylactic shock was sustained.

Example 21

Functional Analyses of Anionic Oligosaccharide Conjugates on the Asthma Target Protein, IL-13

The various anionic oligosaccharide conjugates inhibited the proliferation of an IL-13 responsive cell line to differing degrees. This occurs at very low doses and is believed not to be due to a toxic effect of the anionic oligosaccharide conjugate because other, similarly sulfated polysaccharides, at the same concentrations of IL-13 and polysaccharide have no effect. These experiments utilize the TF-1 cells that are grown in GM-CSF. TF-1 cells were originally established from a bone marrow sample from a male with severe pancytopenia. These cells are dependent on IL-3 or GM-CSF for long term growth and are responsive to a variety of cytokines including IL-13.

Briefly, proliferation assays were carried out in 96-well microplates suitable for such assays. Cells were washed to remove any cytokine in the growth medium and then resuspended in RPMI/5% w/v FCS and routinely $2.5 \times 10^4$ cells were added to microplate wells that contain either no IL-13 (negative control) or various dilutions of IL-13. When the effect of the different sized sulfated xylans was measured, the wells also contained various concentrations of these molecules and the IL-13 concentration was held constant at 2.5 ng/ml. The cells proliferated for 48 hours, after which the number of cells present was quantified by staining with 20 μL per well of the AQUEOUS ONE dye for 3 hours and then absorbance was read at 490 nm.

The saccharide component of the anionic oligosaccharide conjugate seems to be important for activity. Both the size of the oligosaccharide and the underlying composition seems to be important. The linked pentasaccharides are more effective inhibitors than linked tetrasaccharides and, of the linked pentasaccharides, the linked sulfated maltose series was the most effective but the linked sulfated xylan pentasaccharides also displayed some activity. All conjugates of the chitosan series had low activity indicating this backbone is ineffective for constructing anionic conjugates that inhibit IL-13. Interestingly, a linked sulfated maltotetraose anionic oligosaccharide conjugate with the smallest linker (Et1) displayed similar activity to that of the linked sulfated maltopentaose with an Et1 linker, but those linked sulfated maltotetraoses with longer linkers had reduced activity. Thus, it appeared that closely linked sulfated tetrasaccharides of the maltose series is sufficient for activity, but closely linked trisaccharides had little activity. The best anionic oligosaccharide conjugate was of the maltose series with an Et4 linker suggesting clusters of sulfated residues displayed on a maltose pentasaccharide backbone separated by a non-sulfated, non-saccharide region is preferred.

TABLE 9

The ability of the anionic oligosaccharide conjugates
to inhibit IL-13 dependent cell proliferation

| | | | % Inhibition of TF1 cell proliferation stimulated by IL-13 | |
|---|---|---|---|---|
| ID | Persulfated oligosaccharide | Linker | Anionic oligosaccharide conjugate (2.5 µg/mL) | Anionic oligosaccharide conjugate (10 µg/mL) |
| 1 | Maltotriose | Et1 | 29 ± 2.2 | 43.8 ± 4.2 |
| 2 | Maltotriose | Et2 | | |
| 3 | Maltotriose | Et3 | 26 ± 3.5 | 26.4 ± 9.5 |
| 4 | Maltotriose | Et4 | 31.5 ± 4.9 | 46 ± 1.9 |
| 5 | Maltotriose | Et5 | 25.5 ± 1.9 | 45.4 ± 6.2 |
| 6 | Maltopentaose | Et1 | 48.1 ± 8.7 | 72 ± 3.4 |
| 7 | Maltopentaose | Et2 | 39.8 ± 4.5 | 88.7 ± 1 |
| 8 | Maltopentaose | Et3 | 44.2 ± 4.6 | 89 ± 2.1 |
| 9 | Maltopentaose | Et4 | 49.6 ± 6.4 | 94.1 ± 3.7 |
| 10 | Maltopentaose | Et5 | 47.7 ± 0.9 | 83 ± 1.2 |
| 11 | Maltotetraose | Et1 | 52.5 ± 1.6 | 80.7 ± 3 |
| 12 | Maltotetraose | Et2 | 29.6 ± 5.8 | 63.1 ± 4.6 |
| 13 | Maltotetraose | Et3 | 39.5 ± 1.9 | 37.4 ± 9.5 |
| 14 | Maltotetraose | Et4 | 32 ± 7 | 52.9 ± 5.5 |
| 15 | Maltotetraose | Et5 | | |
| 66 | Chitotetraose | Et1 | 11.9 ± 6.1 | 31.4 ± 0.8 |
| 67 | Chitotetraose | Et2 | 4.8 ± 1.8 | 29 ± 6.8 |
| 68 | Chitotetraose | Et3 | −4.3 ± 4.8 | 23.5 ± 14.6 |
| 69 | Chitotetraose | Et5 | 4.3 ± 7.8 | 25.7 ± 9.9 |
| 70 | Chitopentaose | Et1 | 4.7 ± 7.2 | 34.7 ± 17.5 |
| 71 | Chitopentaose | Et2 | 4 ± 3.3 | 22 ± 2.2 |
| 72 | Chitopentaose | Et3 | 7 ± 4.4 | 20.6 ± 3.5 |
| 73 | Chitopentaose | Et4 | −3.8 ± 1.8 | 25 ± 7 |
| 74 | Chitopentaose | Et5 | 5.6 ± 3.2 | 20.5 ± 6.1 |
| 75 | Xylotetraose | Et1 | 35.8 ± 4.2 | 61.1 ± 2.2 |
| 76 | Xylotetraose | Et2 | 30.5 ± 2.7 | 56.5 ± 8.2 |
| 77 | Xylotetraose | Et3 | 36 ± 1.8 | 55 ± 2.5 |
| 78 | Xylotetraose | Et4 | 38.2 ± 2.3 | 53.2 ± 0.8 |
| 79 | Xylotetraose | Et5 | 22.9 ± 4.1 | 41.1 ± 5.8 |
| 80 | Xylopentaose | Et1 | 42.8 ± 3 | 61.3 ± 5 |
| 81 | Xylopentaose | Et2 | 40.8 ± 9.5 | 63.5 ± 9.5 |
| 82 | Xylopentaose | Et3 | 32.5 ± 4.2 | 65.7 ± 2.6 |
| 83 | Xylopentaose | Et4 | 37.2 ± 0.8 | 62 ± 3.4 |
| 84 | Xylopentaose | Et5 | 35.8 ± 7.7 | 69.8 ± 3.8 |

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. An anionic oligosaccharide conjugate of formula (I):

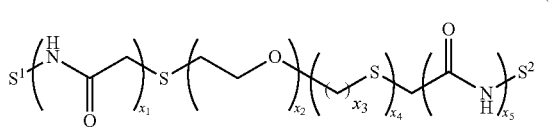

(I)

wherein:

S$^1$ and S$^2$ are each independently a residue of an anionic oligosaccharide bearing a free reducing terminus which is an amino group;

$x_1$ is an integer from 1 to 4;

$x_2$ is an integer from 0 to 11;

$x_3$ is an integer from 0 to 10;

$x_4$ is 0 or 1; and $x_5$ is an integer from 1 to 4.

2. The anionic oligosaccharide conjugate according to claim 1 wherein S$^1$ and S$^2$ are covalently bound to the conjugate through the reducing terminus of the anionic oligosaccharide.

3. The anionic oligosaccharide conjugate according to claim 1 or claim 2 wherein $x_1$ and/or $x_5$ are 1 or 2.

4. The anionic oligosaccharide conjugate according claim 1 or claim 2 wherein $x_1$ and/or $x_5$ are 2.

5. The anionic oligosaccharide conjugate according to claim 1 wherein $x_3$ is 2.

6. The anionic oligosaccharide conjugate according to claim 1 wherein $x_4$ is 1.

7. The anionic oligosaccharide conjugate according to claim 1 wherein S$^1$ and S$^2$ are independently selected from a residue of maltotriose, maltotetraose, maltopentaose, xylotetraose, xylopentaose, chitotetraose and chitopentaose which each comprise at least one anionic substituent.

8. The anionic oligosaccharide conjugate according to claim 1 wherein $x_2$ is an integer from 0 to 4.

9. The anionic oligosaccharide conjugate according to claim 1 wherein $x_3$ is an integer from 2 to 6.

10. A process for preparing an anionic oligosaccharide of formula (I):

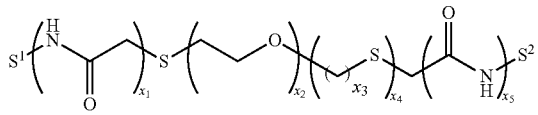

according to claim 1;
the process comprising the steps of:
a) transforming each of the oligosaccharides into anionic oligosaccharides; and
b) conjugating the oligosaccharides;
wherein steps a) and b) may be performed in either order.

11. A method of preventing and/or treating an inflammatory respiratory disorder comprising administering to a subject in need thereof a therapeutically effective amount of an anionic oligosaccharide of formula (I):

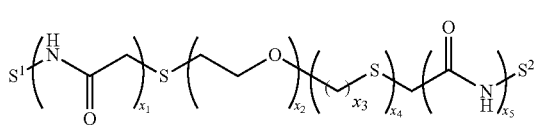

according to claim 1.

12. The method according to claim 11 wherein the inflammatory respiratory disorder is selected from anaphylaxis, asthma, allergic respiratory disease, allergic rhinitis, subepithelial fibrosis in airway hyperresponsiveness, chronic sinusitis, perennial allergic rhinitis, allergic bronchopulmonary aspergillosis in cystic fibrosis patients, COPD, ARDS/ALI, eosinophilic bronchitis, brochiectasis, bronchospasm, bronchial constriction, bronchial hyperreactivity, bronchial hypertrophy or bronchial inflammation.

13. The anionic oligosaccharide conjugate according to claim 1 wherein the anionic oligosaccharide conjugate further comprises a composition with one or more pharmaceutically acceptable excipients.

14. An assay or screen for determining the biological effect of one or more anionic oligosaccharide conjugates, the assay comprising the steps of:
a) contacting a ligand, cell or animal with one or more anionic oligosaccharide conjugates each independently having the following formula (I):

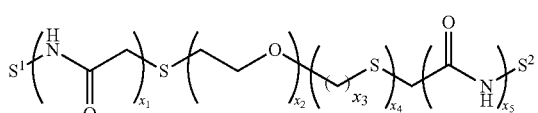

according to claim 1; and b) quantifying an effect of the one or more anionic oligosaccharide conjugates on the ligand, cell or animal.

15. Method of modulating the activity of a ligand comprising contacting the ligand with an anionic oligosaccharide conjugate of formula (I):

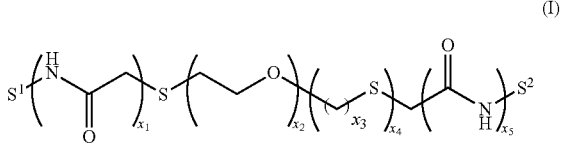

according to claim 1.

16. The method according to claim 15 wherein the ligand is a peptide, polypeptide, protein, carbohydrate, lipid, glycoprotein or a molecule obtained from natural product screening or from a chemical library.

17. The method according to claim 15 wherein the ligand is a protein which binds to a glycosaminoglycan selected from heparin, heparin sulphate, chondroitin and hyaluronan.

18. The method according to claim 15 wherein the protein is selected from histamine, a cytokine, an interferon, a growth factor, an enzyme, a chemokine or a soluble or cell- or virus-bound receptor.

19. The method according to claim 18 wherein the cytokine is an interleukin selected from IL-1, IL-2, IL-3, IL-4, IL-5, IL-6, IL-7, IL-8, IL-9, IL-10, IL-11, IL-12, IL-13, IL-14, IL-15, or a member of the IL-17 family including IL-25.

20. The method according to claim 18 wherein the interferon is selected from α-interferon, β-interferon and γ-interferon.

21. The method according to claim 18 wherein the growth factor is selected from G-CSF, M-CSF, GM-CSF, BDNF, CNTF, EGF, EPO, FGF1, FGF2, FGF3, FGF4, FGF5, FGF6, FGF7, FGF8, FGF9, FGF10, FGF11, FGF12, FGF12, FGF13, FGF14, FGF15, FGF16, FGF17, FGF18, FGF19, FGF20, FGF21, FGF22, FGF23, LIF, MCPJ, MCP2, MCP3, MCP4, MCPS, M-CSF, MIP1, MIP2, KC, NGF, NT 3, NT4, NTS, NT6, NT7, OSM, PBP, PBSF, PDGF, PECAM-1, PF4, RANTES, SCF, TGFα, TGFβ$_1$, TGFβ$_2$, TGFβ$_3$, TNFα, TNFβ, TPO, VEGF, GH and insulin.

22. The method according to claim 18 wherein the enzyme is selected from superoxide dismutase, eosinophilic cationic protein, a tryptase (including β-tryptase), a chymase, an elastase, phospholipase A2 or prostaglandin endoperoxide.

23. The method according to claim 18 wherein the chemokine is selected from eotaxin-1, eotaxin-2 or eotaxin-3.

24. The method according to claim 18 wherein the soluble or cell- or virus-bound receptor is an inositol triphosphate receptor.

25. The method according to claim 15 wherein the modulation is inhibition.

\* \* \* \* \*

UNITED STATES PATENT AND TRADEMARK OFFICE
CERTIFICATE OF CORRECTION

PATENT NO. : 8,597,632 B2  Page 1 of 1
APPLICATION NO. : 13/122427
DATED : December 3, 2013
INVENTOR(S) : Kett et al.

It is certified that error appears in the above-identified patent and that said Letters Patent is hereby corrected as shown below:

In the Claims

Column 60, Line 44, Claim 21:

After "LIF" delete "MCPJ" and
Insert -- MCP1 --.

Column 60, Line 45, Claim 21:

After "MCP4" delete "MCPS" and
Insert -- MCP5 --.

Column 60, Line 45-46, Claim 21:

After "NT4" delete "NTS" and
Insert -- NT5 --.

Signed and Sealed this
Tenth Day of June, 2014

Michelle K. Lee
*Deputy Director of the United States Patent and Trademark Office*